United States Patent
Loerner et al.

(10) Patent No.: US 12,226,348 B2
(45) Date of Patent: Feb. 18, 2025

(54) SYSTEM AND METHOD OF CORNEAL CROSS-LINKING

(71) Applicant: ALCON INC., Fribourg (CH)

(72) Inventors: Johannes Loerner, Roßtal (DE); Peter Riedel, Nuremberg (DE); Linda Weise, Erlangen (DE)

(73) Assignee: ALCON INC., Fribourg (CH)

( * ) Notice: Subject to any disclaimer, the term of this patent is extended or adjusted under 35 U.S.C. 154(b) by 0 days.

(21) Appl. No.: 17/120,842

(22) Filed: Dec. 14, 2020

(65) Prior Publication Data
US 2021/0177651 A1 Jun. 17, 2021

Related U.S. Application Data

(60) Provisional application No. 62/947,772, filed on Dec. 13, 2019.

(51) Int. Cl.
*A61F 9/008* (2006.01)

(52) U.S. Cl.
CPC ........ *A61F 9/0084* (2013.01); *A61F 9/00836* (2013.01); *A61F 2009/00846* (2013.01); *A61F 2009/00848* (2013.01); *A61F 2009/00853* (2013.01); *A61F 2009/00872* (2013.01); *A61F 2009/00893* (2013.01)

(58) Field of Classification Search
CPC .............. A61F 9/00827; A61F 9/00836; A61F 2009/00872; A61F 2009/00846; A61F 2009/00842; A61F 2009/00853; A61N 5/062
USPC ......................................................... 606/4–6
See application file for complete search history.

(56) References Cited

U.S. PATENT DOCUMENTS

| | | | | |
|---|---|---|---|---|
| 4,718,418 | A * | 1/1988 | L'Esperance, Jr. | B23K 26/082 219/121.75 |
| 6,210,401 | B1 * | 4/2001 | Lai | B23K 26/032 606/4 |
| 6,325,792 | B1 * | 12/2001 | Swinger | A61F 9/00834 606/4 |
| 7,146,983 | B1 * | 12/2006 | Hohla | A61B 5/117 606/4 |
| 9,707,126 | B2 | 7/2017 | Friedman et al. | |
| 2005/0024586 | A1 * | 2/2005 | Teiwes | A61B 3/113 351/209 |

(Continued)

FOREIGN PATENT DOCUMENTS

| CA | 2840256 A1 | 12/2012 |
|---|---|---|
| CA | 13133258 A1 | 12/2012 |

(Continued)

*Primary Examiner* — James M Kish
*Assistant Examiner* — Roland Dinga

(57) ABSTRACT

The disclosure provides a system that may: receive data associated with multiple locations associated with a cornea of an eye; adjust at least one lens, based at least on diameter information of the data associated with at least one of the multiple locations, to set a diameter of a laser beam; and for each location of the multiple locations: determine if the eye has changed from a first position to a second position; if the eye has not changed from the first position to the second position, adjust, based at least on the location, at least one mirror; if the eye has changed from the first position to the second position, adjust, based at least on the location and based at least on the second position, the at least one mirror; produce the laser beam; and direct the laser beam to the location for a period of time.

19 Claims, 20 Drawing Sheets

(56) References Cited

U.S. PATENT DOCUMENTS

| | | | |
|---|---|---|---|
| 2005/0119642 A1* | 6/2005 | Grecu | A61F 9/00804 606/5 |
| 2007/0225595 A1* | 9/2007 | Malackowski | A61B 5/064 600/424 |
| 2010/0057059 A1 | 3/2010 | Makino | |
| 2010/0210996 A1* | 8/2010 | Peyman | A61F 9/0079 604/20 |
| 2010/0324542 A1 | 12/2010 | Kurtz | |
| 2012/0150160 A1* | 6/2012 | Vogler | A61F 9/00836 606/4 |
| 2012/0215155 A1* | 8/2012 | Muller | A61F 9/0079 604/20 |
| 2013/0116757 A1* | 5/2013 | Russmann | A61F 9/008 607/89 |
| 2013/0338650 A1* | 12/2013 | Jester | A61F 9/008 606/5 |
| 2015/0313756 A1 | 11/2015 | Skerl et al. | |
| 2017/0100282 A1 | 4/2017 | Seiler | |
| 2017/0280989 A1* | 10/2017 | Heeren | A61B 34/20 |
| 2018/0021172 A1* | 1/2018 | Zheleznyak | A61F 9/00814 606/5 |

FOREIGN PATENT DOCUMENTS

| | | |
|---|---|---|
| CN | 105517514 A | 4/2016 |
| DE | 102015013237 A1 | 4/2017 |
| EP | 2574318 A1 | 4/2013 |
| JP | 2008136501 A | 6/2008 |
| JP | 2013078399 A | 5/2013 |
| JP | 2017505190 A | 2/2017 |
| WO | 9308877 A1 | 5/1993 |
| WO | 2013126838 A2 | 8/2013 |
| WO | 2014172621 A2 | 10/2014 |
| WO | 2015119892 A1 | 8/2015 |

* cited by examiner

SYSTEM AND METHOD OF CORNEAL CROSS-LINKING

BACKGROUND

Field of the Disclosure

This disclosure relates to corneal cross-linking.

Description of the Related Art

In the past, corneal cross-linking (CXL) was used as a treatment for keratoconus. With this condition, a cornea of an eye of a patient thins and becomes weaker over time. Sometimes another condition can cause a similar weakening of the cornea. The weakened cornea can bulge into a cone shape or some irregular shape. The cone shape can distort vision of the eye. If the cornea continues to weaken and/or becomes too thin, a corneal transplant may be performed on the eye. With CXL, a doctor can use riboflavin and ultraviolet (UV) light to make tissue of the cornea stronger. The source of the UV light has been an UV lamp, and the UV lamp can produce the UV light for an amount of time. CXL can add bonds between collagen fibers of the cornea. The bonds between the collagen fibers can aid in stabilizing the cornea. When the tissue of the cornea become stronger, the cornea may have additional one or more bulges and/or may reduce one or more risks of a rupture in the cornea. CXL can mitigate or stop progressive keratoconus from becoming worse.

SUMMARY

The present disclosure provides a system that may receive data associated with multiple locations associated with a cornea of an eye of a patient and may adjust at least one lens, based at least on diameter information of the data associated with at least one of the multiple locations, to set a diameter of a laser beam. The system may include a laser that generates the laser beam. The laser beam may be an ultraviolet (UV) laser beam. A first portion of the cornea may be associated with the multiple locations. A second portion of the cornea, different from the first portion, may not be associated with the multiple locations. The system, for each location of the multiple locations, may further determine if the eye has changed from a first position to a second position, different from the first position; if the eye has not changed from a first position to a second position, may further adjust, based at least on the location, at least one mirror; if the eye has changed from the first position to the second position, may further adjust, based at least on the location and based at least on the second position, the at least one mirror; may further produce the laser beam; and may further direct the laser beam to the location for a period of time associated with the location.

To determine if the eye has changed from the first position of the eye to the second position of the eye, the system may further determine if an iris structure of the eye has changed from a first position of the iris structure to a second position of the iris structure. To produce the laser, the system may pulse the laser beam at a pulse duration. For example, the pulse duration may be a microsecond duration, a nanosecond duration, a picosecond duration, a femtosecond duration, or an attosecond duration, among others. A first period of time associated with a first location of the multiple locations may be different from a second period of time associated with a second location of the multiple locations, different from the first location. The system may further adjust the at least one lens, based at least on second diameter information of the data associated with at least another one of the multiple locations, to set a second diameter of the laser beam. The system may further, if the eye has changed from the first position of the eye to the second position of the eye, translate at least two of the multiple locations based at least on the first position of the eye and the second position of the eye. Before the laser beam is produced, the system may further produce another laser beam to cut at least one of a flap and a pocket in the cornea.

The present disclosure further includes a non-transient computer-readable memory device with instructions that, when executed by a processor of a system, cause the system to perform the above steps. The present disclosure further includes a system and/or a non-transient computer-readable memory device as described above with one or more of the following features, which may be used in combination with one another unless clearly mutually exclusive: i) receive data associated with multiple locations associated with a cornea of an eye of a patient; ii) adjust at least one lens, based at least on diameter information of the data associated with at least one of the multiple locations, to set a diameter of a laser beam; iii) determine if the eye has changed from a first position of the eye to a second position of the eye, different from the first position of the eye; iv) if the eye has not changed from the first position of the eye to the second position of the eye, adjust, based at least on the location, at least one mirror; v) if the eye has changed from the first position of the eye to the second position of the eye, adjust, based at least on the location and based at least on the second position of the eye, the at least one mirror; vi) produce the laser beam; vii) direct the laser beam to the location for a period of time associated with the location; viii) determine if an iris structure of the eye has changed from a first position of the iris structure to a second position of the iris structure; ix) pulse the laser beam at a pulse duration; x) adjust the at least one lens, based at least on second diameter information of the data associated with at least another one of the multiple locations, to set a second diameter of the laser beam; xi) if the eye has changed from the first position of the eye to the second position of the eye, translate at least two of the multiple locations based at least on the first position of the eye and the second position of the eye; and xii) before the laser beam is produced, produce another laser beam to cut at least one of a flap and a pocket in the cornea.

Any of the above systems may be able to perform any of the above methods and any of the above non-transient computer-readable memory devices may be able to cause a system to perform any of the above methods. Any of the above methods may be implemented on any of the above systems or using any of the above non-transient computer-readable memory devices.

It is to be understood that both the foregoing general description and the following detailed description are examples and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

For a more complete understanding of the present disclosure and its features and advantages, reference is now made to the following description, taken in conjunction with the accompanying drawings, which are not drawn to scale, and in which.

DETAILED DESCRIPTION

Figure 1A:
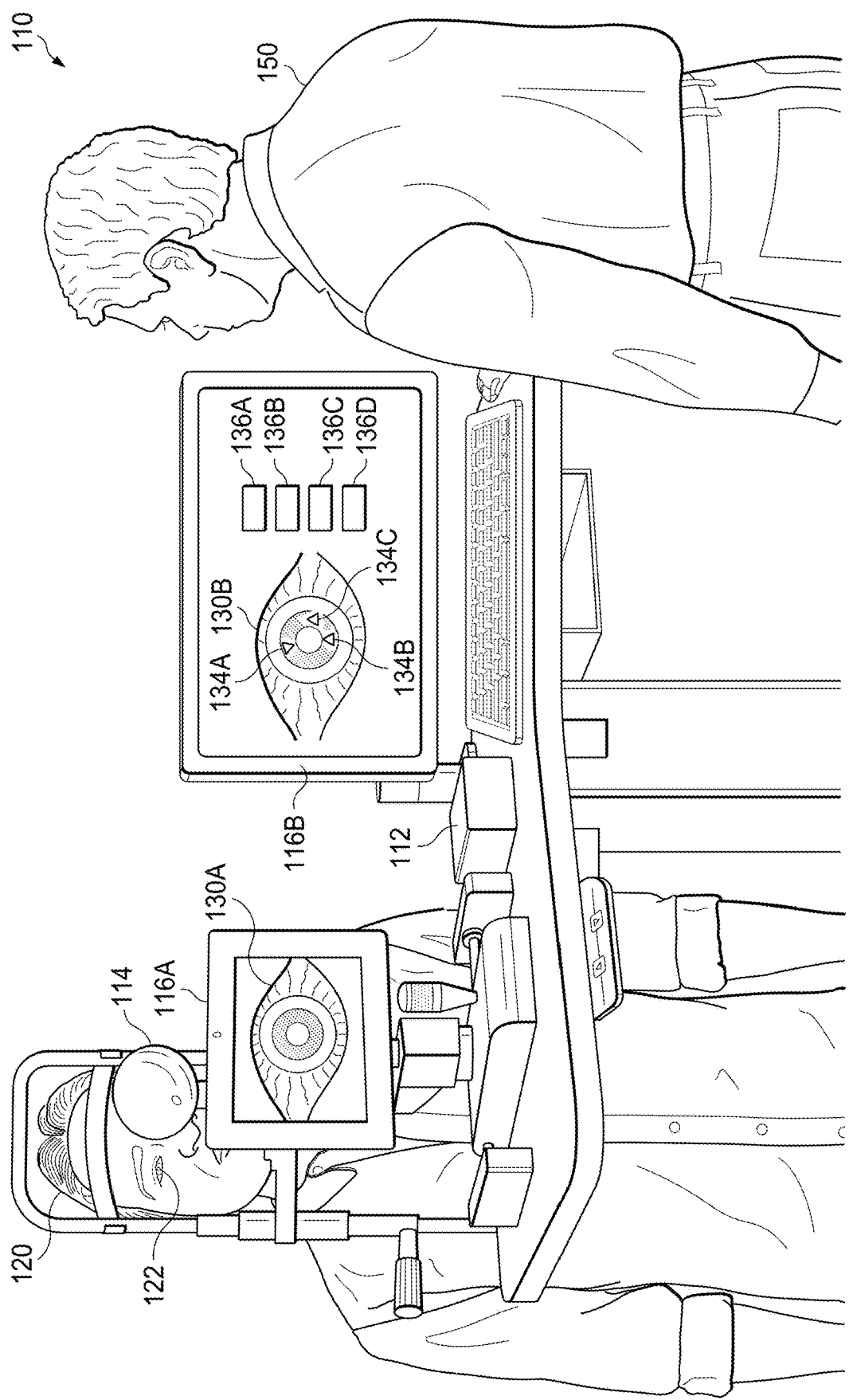
FIG. 1A illustrates an example of a medical system.

In the following description, details are set forth by way of example to facilitate discussion of the disclosed subject matter. It should be apparent to a person of ordinary skill in the field, however, that the disclosed embodiments are examples and not exhaustive of all possible embodiments.

As used herein, a reference numeral refers to a class or type of entity, and any letter following such reference numeral refers to a specific instance of a particular entity of that class or type. Thus, for example, a hypothetical entity referenced by '12A' may refer to a particular instance of a particular class/type, and the reference '12' may refer to a collection of instances belonging to that particular class/type or any one instance of that class/type in general.

Medical systems may be utilized in performing medical procedures with patients. In one example, a first medical system may be utilized, at a first time, in identifying one or more portions of a patient before a medical procedure. In a second example, a second medical system may be utilized, at a second time, in performing the medical procedure. In another example, the second medical system may utilize, at the second time, one or more identifications respectively associated with the one or more portions of the patient. The second time may be a later time than the first time. In one example, the first medical system may be utilized at an office of a doctor. In a second example, the second medical system may be utilized at a surgical facility. In another example, the second medical system may be utilized at the office of the doctor.

Medical systems may include optics. For example, a medical system may include one or more optical systems that may include optics. An optical system may include one or more optical devices. For example, an optical device may be or may include a device that controls light (e.g., reflects light, refracts light, filters light, transmits light, polarizes light, etc.). An optical device may be made of any material that controls the light as designed. For example, the material may include one or more of glass, crystal, metal, and semiconductor, among others. Examples of optical devices may include one or more of lenses, mirrors, prisms, optical filters, waveguides, waveplates, beam expanders, beam collimators, beam splitters, gratings, and polarizers, among others.

A medical procedure may include corneal cross-linking (CXL). CXL may be utilized in treating a condition and/or an issue of a cornea of an eye. The condition and/or the issue may cause the cornea to become weakened and/or thinned over time. For example, the condition and/or the issue may be keratoconus. CXL may be achieved via utilization of an ultraviolet (UV) laser. A laser may be or include a device that generates a beam of coherent monochromatic light by stimulated emission of photons from excited atoms and/or molecules. The UV laser may be pulsed. For example, pulses of a laser beam may have a pulse duration in any suitable range, e.g., the microsecond, nanosecond, picosecond, femtosecond, or attosecond range, among others. An UV laser beam may be directed to one or more locations associated with the cornea. For example, directing the UV laser beam to the one or more locations associated with the cornea may include adjusting at least one mirror to direct the UV laser beam to the one or more locations associated with the cornea. One or more locations associated with the cornea may be utilized in treating the cornea. A diameter of the UV laser beam may be adjustable. For example, a beam expander may be utilized to adjust a diameter of the UV laser beam.

Each of at least two of multiple locations associated with the cornea may be associated with an intensity profile. In one example, a first location associated with the cornea may be associated with a first intensity profile. The first intensity profile may be associated with a first optical intensity of a laser beam. In another example, a second location, different from the first location, associated with the cornea may be associated with a second intensity profile, different from the first intensity profile. The second intensity profile may be associated with a second optical intensity of the laser beam, different from the first optical intensity of the laser beam. An optical intensity of a laser beam may be an optical power per unit area. For example, the optical power per unit area may be watts per centimeters squared ($W/cm^2$). The optical intensity of the laser beam may be a product of photon energy and photon flux.

Different intensity profiles may be utilized to compensate for intensity losses in certain areas (e.g., at a border of an area). For example, an intensity profile associated with a border of an area may be associated with an optical intensity that is greater than an optical intensity that is with a location that is closer to a center of the area. Different intensity profiles may be utilized to provide increased optical intensities in one or more areas. For example, the increased optical intensities in the one or more areas may enhance one or more CXL effects. Different intensity profiles may be utilized to achieve different effects. For example, the different effects may include one or more refractive change in the cornea. The one or more refractive change in the cornea may be achieved without additional beam shaping apertures and/or without additional optics.

Each of at least two of multiple locations associated with the cornea may be associated with a laser beam diameter. In one example, a first location associated with the cornea may be associated with a first laser beam diameter. In another example, a second location associated with the cornea may be associated with a second laser beam diameter, different from the first laser beam diameter. For example, a beam expander may be utilized to set and/or to configure a laser beam diameter. An angle of a laser beam expansion may be determined based at least on one or more laser beams parameters. For example, an area of irradiation (e.g., a laser beam diameter) may be determined based at least on a distance between a laser output aperture and an eye of a patient.

Multiple locations associated with the cornea may be associated with a shape and/or a pattern. For example, the multiple locations associated with the cornea may be similar to elements of a shape and/or a pattern. An element of the shape and/or the pattern may be associated with a diameter of a laser beam. An element of the shape and/or the pattern may be associated with a location of a laser beam on the cornea. An element of the shape and/or the pattern may be associated with an amount of photonic irradiation. Two or more elements of the shape and/or the pattern may at least partially overlap. Two or more elements of the shape and/or the pattern may not overlap.

Before and/or during a medical procedure, an eye may change positions and/or may rotate. In one example, if the eye changes positions and/or rotates, a medical system may compensate for position changes and/or for rotation. The medical system may compensate for the position changes and/or for the rotation to direct a laser beam to multiple locations associated with the cornea. In another example, the medical system may alert one or more medical personnel, may cease the medical procedure, and/or may prevent the medical procedure from starting. The medical system may utilize one or more iris structures in determining if the eye changes positions and/or rotates.

A first medical system may determine structures of an iris of an eye of a patient. For example, determining the structures of the iris of the eye of the patient may include identifying the structures of the iris of the eye of the patient. A second medical system may utilize the structures of the iris of the eye of the patient to determine if the eye changes positions and/or rotates. The second medical system may utilize a pupil of the eye of the patient to determine if the eye changes positions.

The second medical system may include an UV laser that may be utilized in one or more CXL medical procedures. The second medical system may include a laser (e.g., an UV laser, a visible spectrum laser, an infrared laser, etc.) that may cut a pocket in the eye. The position of an incision for the pocket may be associated with a location on the eye. As an example, the second medical system and the first medical system may be combined into a single medical system. As another example, the second medical system and the first medical system may be different medical systems.

A CXL medical procedure may be performed after another medical procedure. For example, as a preventative medical procedure, the CXL medical procedure may be performed after a corneal procedure. A laser device may be utilized to perform the corneal procedure and to perform the CXL medical procedure, as an example. The corneal procedure and the CXL medical procedure may be different medical procedures. Utilizing the laser device for the corneal procedure and the CXL medical procedure may reduce an amount of time for the corneal procedure and the CXL medical procedure. Utilizing the laser device for the corneal procedure and the CXL medical procedure may reduce a number of pieces of medical equipment for the corneal procedure and the CXL medical procedure.

Turning now to FIG. 1A, an example of a medical system is illustrated. As shown, a medical system 110 may be utilized with a patient 120. As illustrated, medical system 110 may include a computer system 112. Computer system 112 may be communicatively coupled to displays 116A and 116B. Computer system 112 may be communicatively coupled to a biometry device 114. In one example, biometry device 114 may include one or more cameras. In another example, biometry device 114 may include a three-dimensional scanner. Biometry device 114 may be utilized in biometry of an eye 122 of patient 120. As shown, display 116A may display an image 130A associated with eye 122 of patient 120. As illustrated, display 116B may display an image 130B associated with eye 122 of patient 120.

A user interface may be associated with one or more of computer system 112, display 116A, and display 116B, among others. In one example, a user interface may include one or more of a keyboard, a mouse, a joystick, a touchscreen, an eye tracking device, a speech recognition device, a gesture control module, dials, and/or buttons, among other input devices. In another example, a user interface may include a graphical user interface (GUI). A user (e.g., medical personnel) may enter desired instructions and/or parameters via the user interface.

Computer system 112 may determine eye recognition information. For example, the eye recognition information may include biometry information associated with eye 122 of patient 120. The biometry information associated with eye 122 may include one or more of a pattern of blood vessels of a sclera of eye 122, a structure of an iris of eye 122, a position of a structure of an iris of eye 122, a distance measurement of a cornea of eye 122 to a lens of eye 122, a distance measurement of a lens of eye 122 to a retina of eye 122, a corneal topography of eye 122, a retinal pattern of eye 122, and a wavefront measurement, among others.

As shown, display 116B may display structures 134A-134C of an iris of eye 122. As illustrated, display 116B may display display areas 136A-136D. In one example, display area 136 may display a distance measurement of a cornea of eye 122 to a lens of eye 122, a distance measurement of a lens of eye 122 to a retina of eye 122, a position of an iris structure 134, corneal topography information, or wavefront measurement information, among other biometry information associated with eye 122. In another example, a display area 136 may display any information associated with patient 120.

A person 150 may operate medical system 110. For example, person 150 may be medical personnel. 112. Person 150 may enter identification information associated with patient 120 into computer system 112. The identification information associated with patient 120 may include one or more of a name of patient 120, an address of patient 120, a telephone number of patient 120, a government issued identification number of patient 120, a government issued identification string of patient 120, and a date of birth of patient 120, among others.

Person 150 may provide medical procedure information, associated with patient 120, to computer system 112. The medical procedure information may be associated with a medical procedure. The medical procedure information may be associated identification information associate with patient 120. Computer system 112 may store the medical procedure information. For example, computer system 112 may store the medical procedure information for later utilization. The medical procedure information may be associated with a surgery. For example, the medical procedure information may be retrieved before the surgery. The medical procedure information may be utilized during a medical procedure. For example, the medical procedure may include a surgery.

Figure 1B:
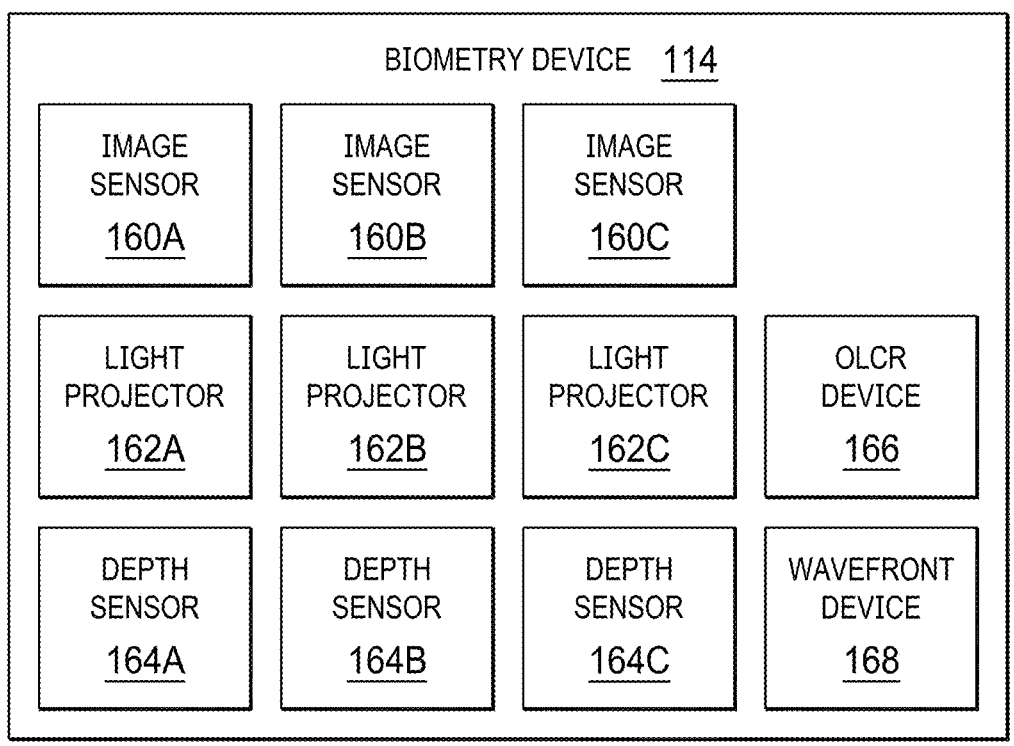
FIG. 1B illustrates an example of a biometry device.

Turning now to FIG. 1B, an example of a biometry device is illustrated. As shown, biometry device 114 may include image sensors 160A-160C. For example, an image sensor 160 may include a camera. A camera may include a one or more digital image sensors. In one example, a digital image sensor may include a charge-coupled device (CCD). In another example, a digital image sensor may include a complementary metal-oxide-semiconductor (CMOS). The camera may transform light into digital data. The camera may utilize a Bayer filter mosaic. For example, the camera may utilize a Bayer filter mosaic in combination with an optical anti-aliasing filter. A combination of the Bayer filter mosaic in combination with the optical anti-aliasing filter may reduce aliasing due to reduced sampling of different primary-color images. The camera may utilize a demosaicing process. For example, the demosaicing process may be utilized to interpolate color information to create a full array of red, green, and blue (RGB) image data.

As illustrated, biometry device 114 may include light projectors 162A-162C. In one example, a light projector 162 may project visible light. In another example, a light projector 162 may project infrared light. A light projector 162 may project circles and/or dots onto an eye of a patient. An image sensor 160 may receive reflections of the circles and/or the dots that were projected onto the eye of the patient. A computer system may determine one or more locations and/or one or more templates associated with the eye of the patient based at least on the reflections of the circles and/or the dots that were projected onto the eye of the patient. As shown, biometry device 114 may include depth sensors 164A-164C. A depth sensor 164 may include a light projector 162. A depth sensor 164 may include an optical sensor. As illustrated, biometry device 114 may include an optical low coherence reflectometer (OLCR) device 166. As shown, biometry device 114 may include a wavefront device 168.

Wavefront device 168 may include one or more of a light source and a wavefront sensor, among others. A light source may provide a first light wave to eye 122. A wavefront sensor may receive a first perturbed light wave, based at least on the first light wave, from eye 122. In one example, wavefront device 168 may determine first optical corrections based at least on the first perturbed light. In another example, a computer system may determine first optical corrections based at least on the first perturbed light. Wavefront device 168 may provide data, based at least on the first perturbed light wave, to a computer system. For example, the computer system may determine first optical corrections based at least on the data from wavefront device 168.

Any two or more of an image sensor 160, a light projector 162, a depth sensor 164, an OLCR device 166, and a wavefront device 168 may be combined. One or more of image sensors 160A-160C, one or more of light projectors 162A-162C, one or more of depth sensors 164A-164C, OLCR device 166, and/or wavefront device 168, among others, may produce data that may be utilized by a computer system.

Figure 2:
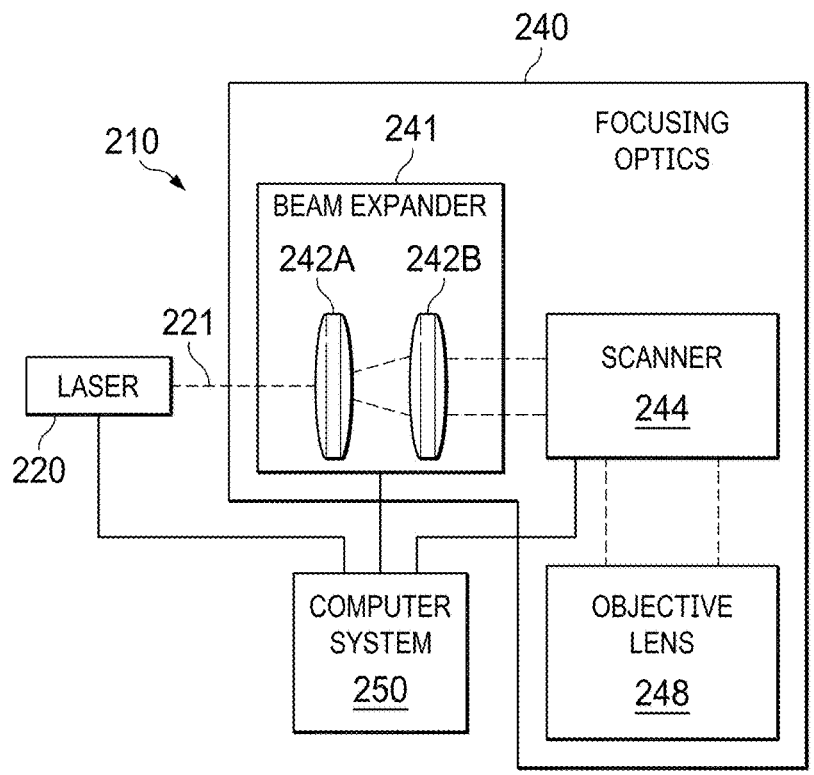
FIG. 2 illustrates an example of a laser system.
Figure 2:
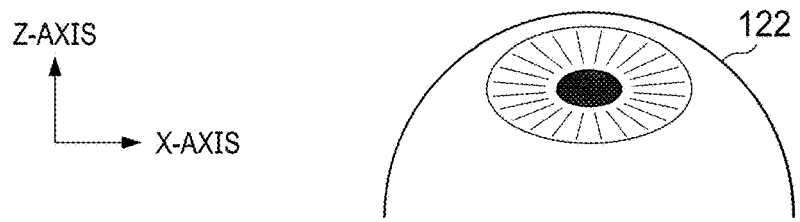

Turning now to FIG. 2, an example of a laser system is illustrated. A laser system 210 may be utilized to irradiate one or more portions of eye 122. For example, laser system 210 may be utilized to irradiate one or more portions of eye 122 with UV light from a UV laser device. Laser system 210 may be utilized in a medical procedure. For example, a medical system may include laser system 210. The medical procedure may include an ophthalmic procedure on at least a portion part of eye 122. Although optical system 210 may be utilized in a medical system, laser system 210 may be utilized in any system.

Laser system 210 may include multiple optical devices. For example, an optical device may be or may include a device that controls light (e.g., reflects light, refracts light, filters light, transmits light, polarizes light, etc.). An optical device may be made of any material that controls the light as designed. For example, the material may include one or more of glass, crystal, metal, and semiconductor, among others. Examples of optical devices may include one or more of lenses, mirrors, prisms, optical filters, waveguides, waveplates, beam expanders, beam collimators, beam splitters, gratings, and polarizers, among others.

As shown, laser system 210 may include a laser 220 (e.g., a laser device). Laser 220 may generate a laser beam 221. In one example, laser 220 may be a device that generates a beam of coherent monochromatic light by stimulated emission of photons from excited atoms and/or molecules. In another example, laser 220 may be a device that generates a laser beam that includes photons associated with multiple frequencies. Laser beam 221 may have any suitable wavelength, e.g., a wavelength in an infrared (IR) range, in a visible range, or in an UV range. Pulses of laser beam 221 may have a pulse duration in any suitable range, e.g., the microsecond, nanosecond, picosecond, femtosecond, or attosecond range, among others. Laser beam 221 may deliver consecutive pulses, having a pulse duration, for a period of time. The focus of laser beam 221 may be a focal point of laser beam 221. Laser beam 221 may represent one or more laser beams. For example, laser 220 may be configured to produce one or more laser beams 221.

As illustrated, laser system may include focusing optics 240. As shown, focusing optics 240 may include a beam expander 241, a scanner 244, and an objective lens 248. Objective lens 248 may include multiple lenses. In one example, objective lens 248 may be or include a compound lens. In another example, objective lens 248 may be or include a F-theta lens. As illustrated, beam expander 241 may include lenses 242A and 242B. Although beam expander 241 is shown with two lenses, beam expander 241 may include any number of lenses.

Focusing optics 240 may direct and/or may focus laser beam 221 towards eye 122. Focusing optics 240 may direct and/or may focus laser beam 221 towards a cornea 310, illustrated in FIG. 3, of eye 122. Focusing optics 240 may direct a focal point of laser beam 221 parallel to or along a Z-axis towards eye 122.

An optical device, such as a lens 242A and/or a mirror, may control a Z-position of a focal point of laser beam 221. Another optical device, such as a lens 242B (e.g., in combination with lens 242A), may expand a diameter of laser beam 221. For example, beam expander 241 may be configured to control a focal point of laser beam 221.

Scanner 244 may include one or more optical devices that may control a direction of laser beam 221 to control a XY-position of the focal point. For example, to transversely deflect laser beam 221, scanner 244 may include a pair of galvanometric actuated mirrors that may tilt about mutually perpendicular axes. Scanner 244 may receive laser beam 221 from beam expander 241. Scanner 244 may manipulate laser beam 221 to control the XY-position of the focal point of laser 221. Objective lens 248 may receive laser beam 221 from the scanner 244. Objective lens 248 may direct laser beam 221 to eye 122.

As illustrated, laser system 210 may include a computer system 250. Computer system 250 may execute instructions in implementing at least a portion of one or more systems, one or more flow charts, one or more processes, and/or one or more methods described herein. Although laser system 210 is illustrated as including computer system 250, laser system 210 may not include computer system 250. For example, computer system 250 may be external to laser system 210. Computer system 250 may be communicatively coupled to laser system 210.

As shown, computer system 250 may be communicatively coupled to laser 220. As illustrated, computer system 250 may be communicatively coupled to beam expander 241. As shown, computer system 250 may be communicatively coupled to scanner 244. In one example, computer system 250 may receive information from one or more of laser 220, beam expander 241, and scanner 244, among others. In another example, computer system 250 may provide information to one or more of laser 220, beam expander 241, and scanner 244, among others. Computer system 250 may provide control information to one or more of laser 220, beam expander 241, and scanner 244, among others.

A medical system may include laser system 210. Laser system 210 may be utilized in one or more medical procedures. As one example, laser system 210 may be utilized with a Dresden protocol. As a second example, laser system 210 may be utilized with a derivation of a Dresden protocol (e.g., higher/lower energy settings, different irradiation times, on/off "pulsed" irradiation, different riboflavin application strategies, etc.). As a third example, laser system 210 may be utilized with created pockets (e.g. corneal pockets, interface after refractive lenticule extraction, LASIK (laser-assisted in situ keratomileusis) flaps, etc.) to apply riboflavin. As another example, laser system 210 may be utilized in a CXL medical procedure.

Figure 3:
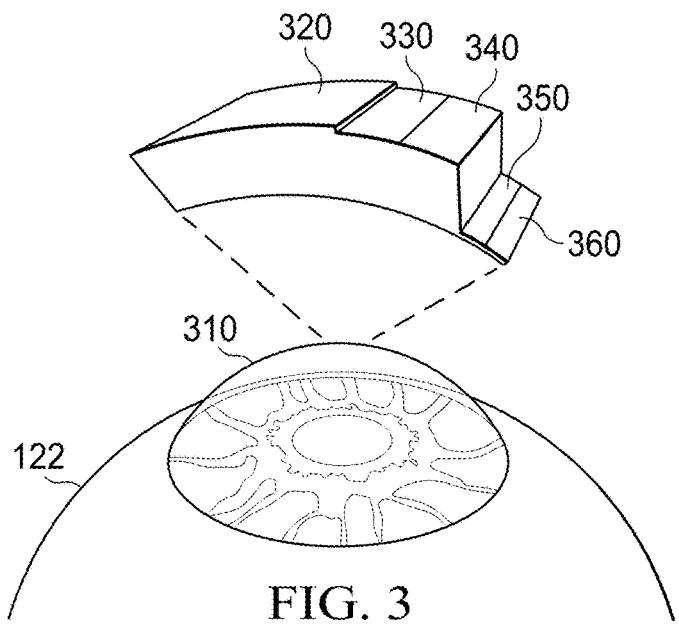
FIG. 3 illustrates an example of layers of a cornea of an eye.

Turning now to FIG. 3, an example of layers of a cornea of an eye is illustrated. As shown, a cornea 310 may include layers 320-360. In one example, layer 320 may be an epithelium. In a second example, layer 330 may be a Bowman's membrane. In a third example, layer 340 may be a stroma. In a fourth example, layer 350 may be a Descemet's membrane. In another example, layer 360 may be an endothelim.

Figure 4A:
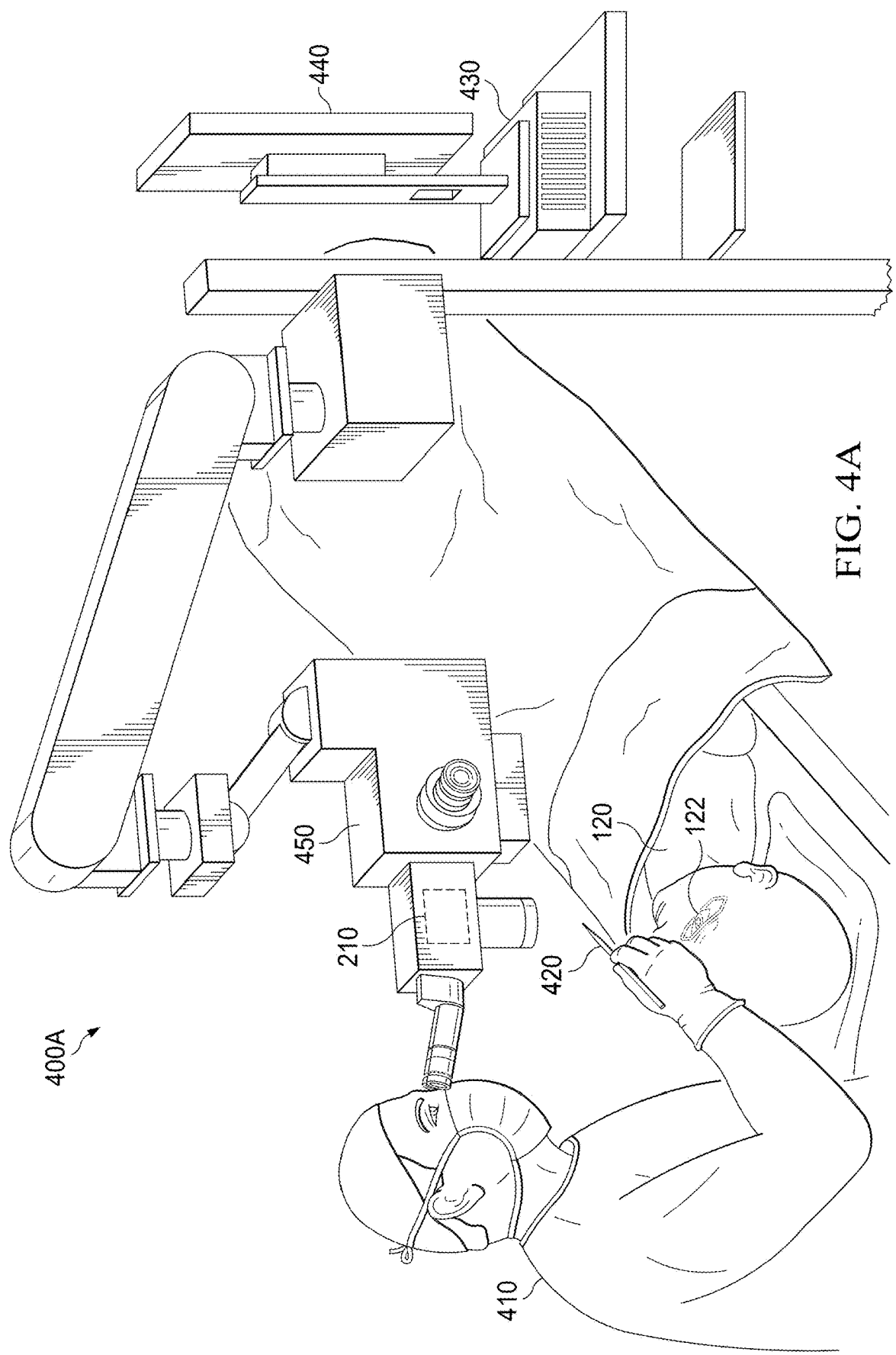
FIG. 4A illustrates a second example of a medical system.

Turning now to FIG. 4A, a second example of a medical system is illustrated. As shown, a surgeon 410 may utilize surgical tooling equipment 420. In one example, surgeon 410 may utilize surgical tooling equipment 420 in a surgery and/or a medical procedure involving eye 122 of patient 120. A medical system 400A may include an ophthalmic surgical tool tracking system. As illustrated, medical system 400A may include a computer system 430, a display 440, and a microscope integrated display (MID) 450.

Computer system 430 may receive image frames captured by one or more image sensors. For example, computer system 430 may perform various image processing on the one or more image frames. Computer system 430 may perform image analysis on the one or more image frames to identify and/or extract one or more images of surgical tooling equipment 420 from the one or more image frames. Computer system 430 may generate a GUI, which may overlay the one or more image frames. For example, the GUI may include one or more indicators and/or one or more icons, among others. The one or more indicators may include medical data, such as one or more positions and/or one or more orientations. The one or more indicators may include one or more warnings. The GUI may be displayed by display 440 and/or MID 450 to surgeon 410 and/or other medical personnel.

Computer system 430, display 440, and MID 450 may be implemented in separate housings communicatively coupled to one another or within a common console or housing. A user interface may be associated with one or more of computer system 430, display 440, and MID 450, among others. For example, a user interface may include one or more of a keyboard, a mouse, a joystick, a touchscreen, an eye tracking device, a speech recognition device, a gesture control module, dials, and/or buttons, among other input devices. A user (e.g., surgeon 410 and/or other medical personnel) may enter desired instructions and/or parameters via the user interface. For example, the user interface may be utilized in controlling one or more of computer system 430, display 440, and MID 450, among others. As illustrated, medical system 400A may include a laser system 210. For example, surgeon 410 may utilize laser system 210 in performing a CXL procedure on eye 122. As an example, MID 450 may include a laser system 210.

Figure 4B:
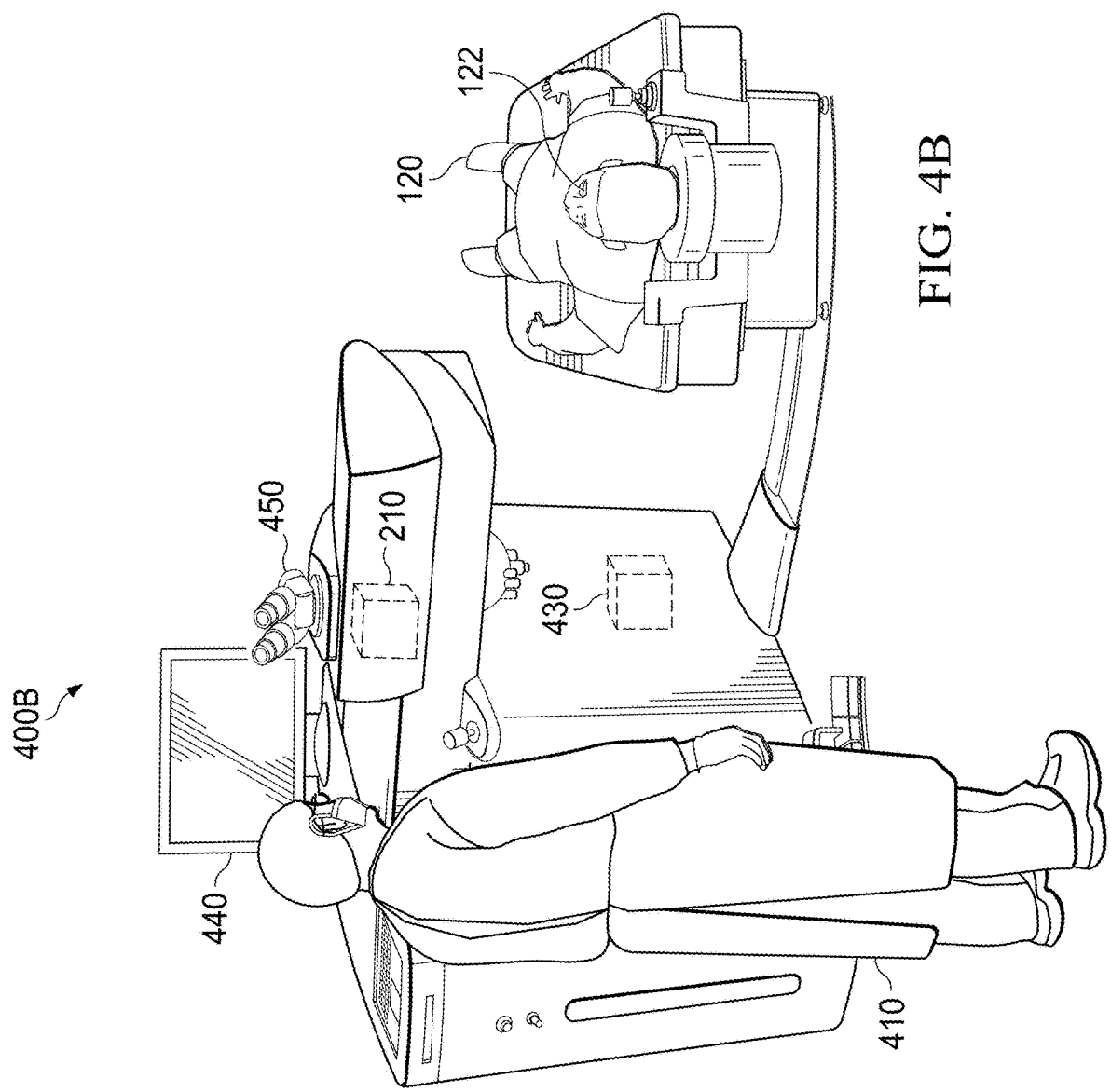
FIG. 4B illustrates a third example of a medical system.

Turning now to FIG. 4B, a third example of a medical system is illustrated. As shown, a surgeon 410 may utilize a system 400B. For example, surgeon 410 may utilize system 400B in a surgery involving eye 122 of patient 120. System 400B may include multiple systems. System 400B may include a cutting system. For example, surgeon 410 may utilize system 400B in cutting eye 122. Surgeon 410 may utilize system 400B in cutting a flap in cornea 310 of eye 122 of patient 120 or in cutting a pocket in cornea 310 of eye 122 of patient 120. In one example, system 400B may cut a flap in cornea 310 of eye 122 with a blade. In a second example, system 400B may cut a pocket in cornea 310 of eye 122 with a blade. In a third example, system 400B may cut a flap in cornea 310 of eye 122 with a laser beam produced by a laser device and/or a laser system. In a fourth example, system 400B may cut a flap in cornea 310 of eye 122 with a laser beam produced by a laser device and/or a laser system. In another example, system 400B may cut any femto-cut in cornea 310 of eye 122 with a laser beam produced by a laser device and/or a laser system. A fluid may be applied to one or more interior portions of cornea 310 of eye 122 via the flap or via the pocket. For example, the fluid may include riboflavin. Surgeon 410 may utilize system 400B in removing a layer from cornea 310 of eye 122. For example, surgeon 410 may utilize system 400B in removing layer 320 from cornea 310 of eye 122. As an example, removing layer 320 may include scraping layer 320 from cornea 310. After layer 320 of cornea 310 of eye 122 is removed, a fluid may be applied to one or more interior portions of the cornea of eye 122. For example, the fluid may include riboflavin.

As illustrated, system 400B may include a laser system 210. For example, surgeon 410 may utilize laser system 210 in performing a CXL procedure on eye 122. As shown, system 400B may include a display 440. As illustrated, system 400B may include a MID 450. System 400B may include one or more of image sensors 160A-160C, one or more of light projectors 162A-162C, one or more of depth sensors 164A-164C, an OLCR device 166, and/or a wavefront device 168, among others.

System 400B may include a laser, such as a femtosecond laser, which may use short laser pulses to ablate or cut a series of small portions of corneal tissue to form a flap that may be lifted up to expose an interior part of cornea 310 of eye 122. The flap may be planned and cut using one or both of display 440 and MID 450, along with control devices and a computer system 430. Fluid may be dispensed under the flap. For example, the fluid may be dispensed to the interior part of cornea 310 of eye 122. The fluid may include riboflavin.

System 400B may include a laser, such as a femtosecond laser, which may use short laser pulses to ablate or cut a series of small portions of corneal tissue to form a pocket that may expose an interior part of cornea 310 of eye 122. The pocket may be planned and cut using one or both of display 440 and MID 450, along with control devices and a computer system 430. Fluid may be dispensed under the pocket. For example, the fluid may be dispensed to the interior part of cornea 310 of eye 122. The fluid may include riboflavin.

As shown, system 400B may include computer system 430. For example, computer system 430 may be communicatively coupled to one or more of image sensors 160A-160C, one or more of light projectors 162A-162C, one or more of depth sensors 164A-164C, an OLCR device 166, a wavefront device 168, display 440, MID 450, a laser, and/or laser system 210, among others, of system 400B.

System 400B may include one or more control devices. For example, the one or more control devices may include one or more of an interactive display, such as a touchscreen display, a keyboard, a mouse, a touchpad, buttons, a joystick, a foot pedal, a heads-up display, and virtual-reality glasses, or other devices able to interact with a user, such as medical personnel.

System 400B may include at least one computer system configured to generate an image presented on at least one of display 440 and MID 450, among others. For example, the at least one computer system may include computer system 430. Computer systems 430 may be communicatively coupled to observational devices, such as a microscope, a camera, an optical coherence tomography (OCT) device or display, or another device able to measure the position of the eye undergoing surgery. Computer systems 430 may be communicatively coupled to one or more of the control devices.

In one example, computer system 430: i) may be communicatively coupled to observational devices that observe eye 122 when patient 120 is positioned with system 400B, ii) may provide graphical information regarding the planned flap location and the planned area of ablation to one or more of display 440 and MID 450, and iii) may be communicatively coupled to one or more control devices of system 400B. In a second example, computer system 430: i) may be communicatively coupled to observational devices that observe eye 122 when patient 120 is positioned with system 400B, ii) may provide graphical information regarding the planned pocket location and the planned area of ablation to one or more of display 440 and MID 450, and iii) may be communicatively coupled to one or more control devices of system 400B. In another example, a computer system may include the properties and/or the attributes described above with respect to computer system 430, among others.

A computer system of a system 400 may be communicatively coupled to another part of system 400 in a wired fashion or in a wireless fashion. One of more of computer systems of system 400 may be communicatively coupled to a database, stored locally, on a remote computer system or a remote data center, or both, that store patient data, treatments plans, and/or other information associated with medical treatments and/or system 400. In one example, the database may include a relational database. In a second example, the database may include a graph database. In another example, the database may include a "Not Only SQL" (NoSQL) database.

System 400 may enter information regarding patient 120 and the treatment to be performed on patient 120 or actually performed on patient 120. System 400 may allow a user to enter and view information regarding patient 120 and the treatment to be performed on patient 120. Such data may include information about patient 120, such as identifying information, a medical history of patient 120, and/or information about eye 122 being treated, among others. Such data may include information about the treatment plans, such as the shape and location of a corneal cut, a shape and location of ablation, and/or multiple locations associated with a CXL procedure, among others.

Figure 4C:
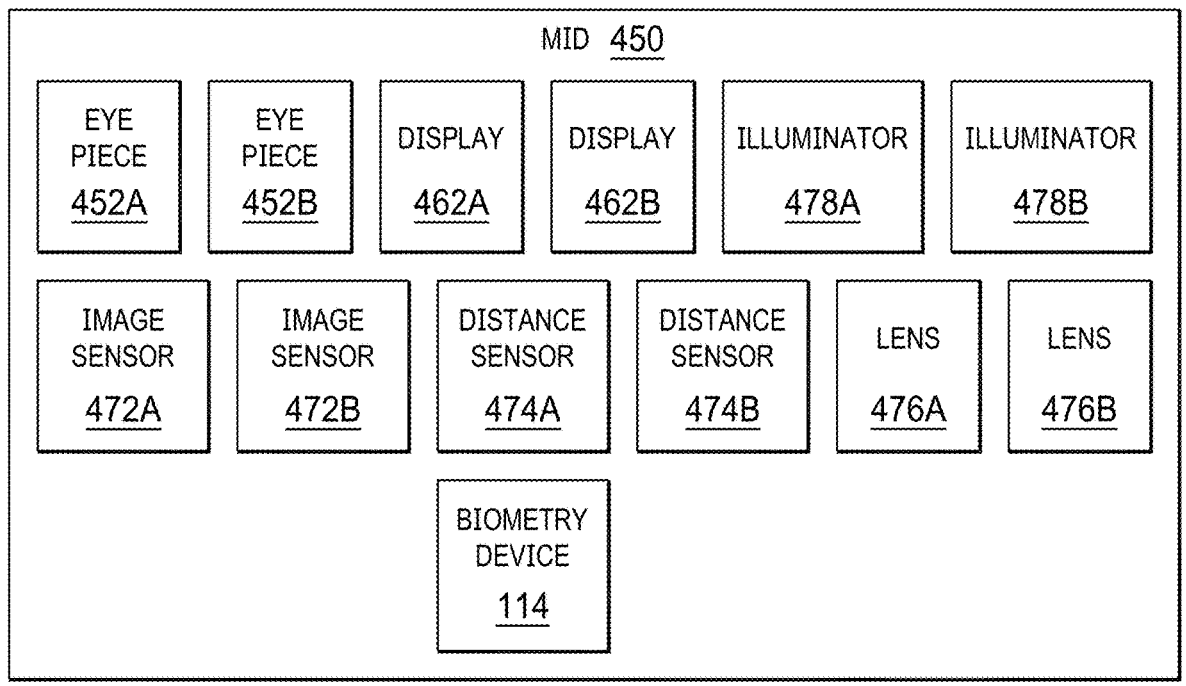
FIG. 4C illustrates an example of a microscope integrated display and examples of surgical tooling equipment.
Figure 4C:
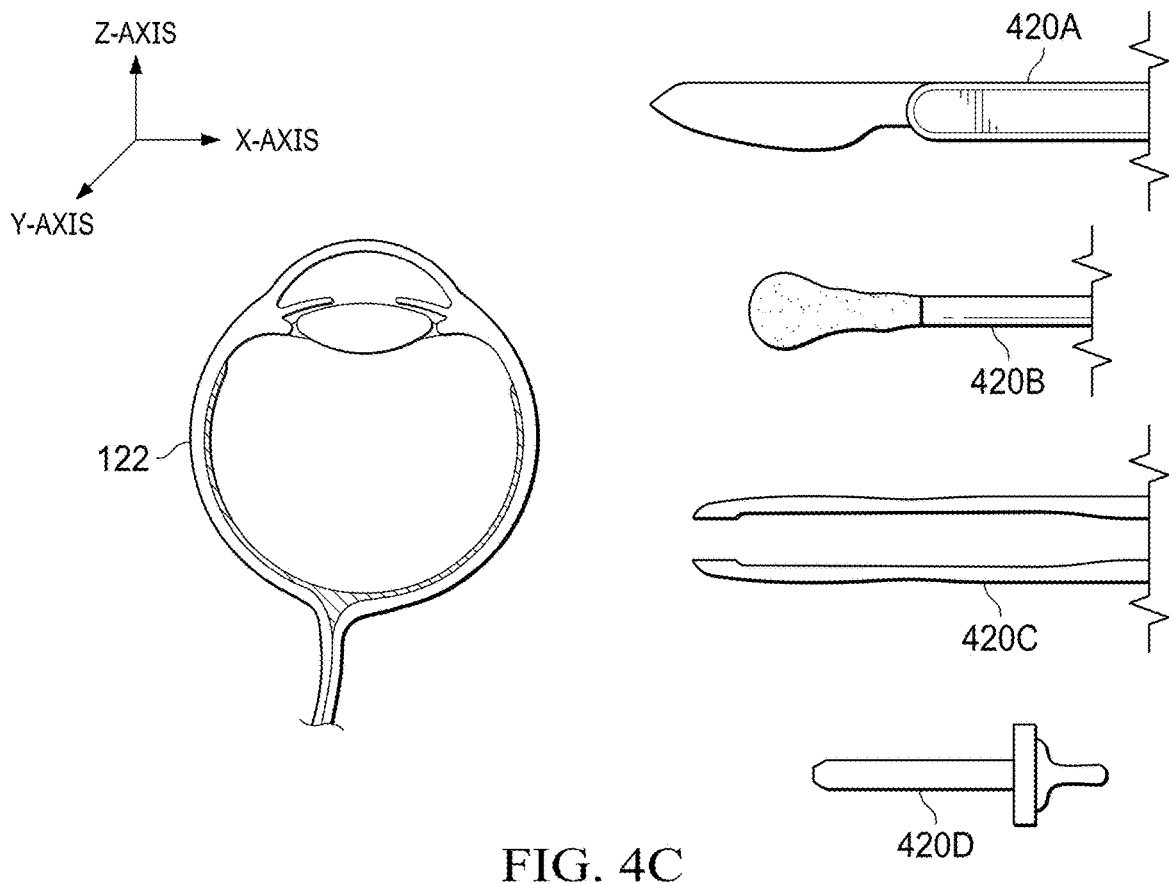

Turning now to FIG. 4C, an example of a microscope integrated display and examples of surgical tooling equipment are illustrated. Medical personnel may utilize surgical tooling equipment 420. As shown, surgical tooling equipment 420A may be or include a scalpel. As illustrated, surgical tooling equipment 420B may be or include a Q-tip. As shown, surgical tooling equipment 420C may be or include tweezers. As illustrated, surgical tooling equipment 420D may be or include an eyedropper. For example, an eyedropper may be utilized to dispense a fluid to eye 122. The fluid may include riboflavin. Other surgical tooling equipment that is not specifically illustrated may be utilized with one or more systems, one or more processes, and/or one or more methods described herein.

As an example, surgical tooling equipment 420 may be marked with one or more patterns. The one or more patterns may be utilized in identifying surgical tooling equipment 420. The one or more patterns may include one or more of a hash pattern, a stripe pattern, and a fractal pattern, among others. As another example, surgical tooling equipment 420 may be marked with a dye and/or a paint. The dye and/or the paint may reflect one or more of visible light, infrared light, and ultraviolet light, among others. In one example, an illuminator 478 may provide ultraviolet light, and image sensor 472 may receive the ultraviolet light reflected from surgical tooling equipment 420. Computer system 430 may receive image data, based at least on the ultraviolet light reflected from surgical tooling equipment 420, from image sensor 472 and may utilize the image data, based at least on the ultraviolet light reflected from surgical tooling equipment 420, to identify surgical tooling equipment 420 from other image data provided by image sensor 472. In another example, an illuminator 478 may provide infrared light, and image sensor 472 may receive the infrared light reflected from surgical tooling equipment 420. Computer system 430 may receive image data, based at least on the infrared light reflected from surgical tooling equipment 420, from image sensor 472 and may utilize the image data, based at least on the infrared light reflected from surgical tooling equipment 420, to identify surgical tooling equipment 420 from other image data provided by image sensor 472.

As illustrated, MID 450 may include eye pieces 452A and 452B. As shown, MID 450 may include displays 462A and 462B. Surgeon 410 may look into eye pieces 452A and 452B. In one example, display 462A may display one or more images via eye piece 452A. A left eye of surgeon 410 may utilize eye piece 452A. In another example, display 462B may display one or more images via eye piece 452B. A right eye of surgeon 410 may utilize eye piece 452B. Although MID 450 is shown with multiple displays, MID 450 may include a single display 462. For example, the single display 462 may display one or more images via one or more of eye pieces 452A and 452B. MID 450 may be implemented with one or more displays 462.

As shown, MID 450 may include image sensors 472A and 472B. In one example, image sensors 472A and 472B may acquire images. In a second example, image sensors 472A and 472B may include cameras. In another example, an image sensor 472 may acquire images via one or more of visible light, infrared light, and ultraviolet light, among others. One or more image sensors 472A and 472B may provide data of images to computer system 430. Although MID 450 is shown with multiple image sensors, MID 450 may include a single image sensor 472. MID 450 may be implemented with one or more image sensors 472.

As illustrated, MID 450 may include distance sensors 474A and 474. For example, a distance sensor 474 may determine a distance to surgical tooling equipment 420. Distance sensor 474 may determine a distance associated with a Z-axis. Although MID 450 is shown with multiple image sensors, MID 450 may include a single distance sensor 474. In one example, MID 450 may be implemented with one or more distance sensors 474. In another example, MID 450 may be implemented with no distance sensor.

As shown, MID 450 may include lenses 476A and 476B. Although MID 450 is shown with multiple lenses 476A and 476B, MID 450 may include a single lens 476. MID 450 may be implemented with one or more lenses 476. As illustrated, MID 450 may include illuminators 478A and 478B. For example, an illuminator 478 may provide and/or produce one or more of visible light, infrared light, and ultraviolet light, among others. Although MID 450 is shown with multiple illuminators, MID 450 may include a single illuminator 478. MID 450 may be implemented with one or more illuminators 478. MID 450 may include one or more devices, one or more structures, and/or one or more functionalities as those described with reference to biometry device 114. In one example, MID 450 may include OLCR device 166. In another example, MID 450 may include wavefront device 168. MID 450 may include a biometry device 114. As shown, MID 450 may include biometry device 114.

Figure 5:
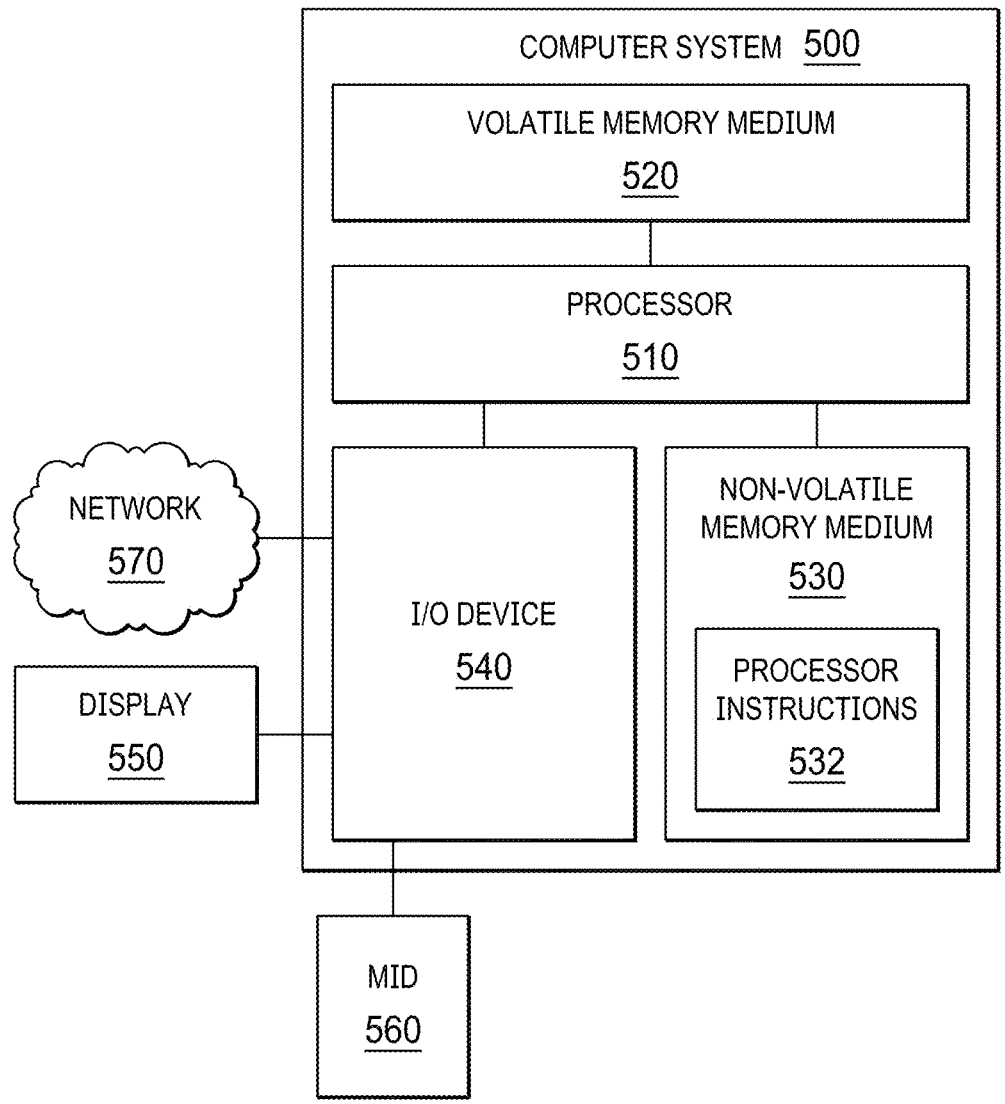
FIG. 5 illustrates an example of a computer system.

Turning now to FIG. 5, an example of a computer system is illustrated. As shown, a computer system 500 may include a processor 510, a volatile memory medium 520, a non-volatile memory medium 530, and an input/output (I/O) device 540. As illustrated, volatile memory medium 520, non-volatile memory medium 530, and I/O device 540 may be communicatively coupled to processor 510.

The term "memory medium" may mean a "memory", a "storage device", a "memory device", a "computer-readable medium", and/or a "tangible computer readable storage medium". For example, a memory medium may include, without limitation, storage media such as a direct access storage device, including a hard disk drive, a sequential access storage device, such as a tape disk drive, compact disk (CD), random access memory (RAM), read-only memory (ROM), CD-ROM, digital versatile disc (DVD), electrically erasable programmable read-only memory (EEPROM), flash memory, non-transitory media, and/or one or more combinations of the foregoing. As shown, non-volatile memory medium 530 may include processor instructions 532. Processor instructions 532 may be executed by processor 510. In one example, one or more portions of processor instructions 532 may be executed via non-volatile memory medium 530. In another example, one or more portions of processor instructions 532 may be executed via volatile memory medium 520. One or more portions of processor instructions 532 may be transferred to volatile memory medium 520.

Processor 510 may execute processor instructions 532 in implementing at least a portion of one or more systems, one or more flow charts, one or more processes, and/or one or more methods described herein. For example, processor instructions 532 may be configured, coded, and/or encoded with instructions in accordance with at least a portion of one or more systems, one or more flowcharts, one or more methods, and/or one or more processes described herein. Although processor 510 is illustrated as a single processor, processor 510 may be or include multiple processors. A processor may include one or more processor cores. One or more of a storage medium and a memory medium may be a software product, a program product, and/or an article of manufacture. For example, the software product, the program product, and/or the article of manufacture may be configured, coded, and/or encoded with instructions, executable by a processor, in accordance with at least a portion of one or more systems, one or more flowcharts, one or more methods, and/or one or more processes described herein.

Processor 510 may include any suitable system, device, or apparatus operable to interpret and execute program instructions, process data, or both stored in a memory medium and/or received via a network. Processor 510 further may include one or more microprocessors, microcontrollers, digital signal processors (DSPs), application specific integrated circuits (ASICs), or other circuitry configured to interpret and execute program instructions, process data, or both.

I/O device 540 may include any instrumentality or instrumentalities, which allow, permit, and/or enable a user to interact with computer system 500 and its associated components by facilitating input from a user and output to a user. Facilitating input from a user may allow the user to manipulate and/or control computer system 500, and facilitating output to a user may allow computer system 500 to indicate effects of the user's manipulation and/or control. For example, I/O device 540 may allow a user to input data, instructions, or both into computer system 500, and otherwise manipulate and/or control computer system 500 and its associated components. I/O devices may include user interface devices, such as a keyboard, a mouse, a touch screen, a joystick, a handheld lens, a tool tracking device, a coordinate input device, or any other I/O device suitable to be used with a system.

I/O device 540 may include one or more busses, one or more serial devices, and/or one or more network interfaces, among others, that may facilitate and/or permit processor 510 to implement at least a portions of one or more systems, processes, and/or methods described herein. In one example, I/O device 540 may include a storage interface that may facilitate and/or permit processor 510 to communicate with an external storage. The storage interface may include one or more of a universal serial bus (USB) interface, a SATA (Serial ATA) interface, a PATA (Parallel ATA) interface, and a small computer system interface (SCSI), among others. In a second example, I/O device 540 may include a network interface that may facilitate and/or permit processor 510 to communicate with a network. I/O device 540 may include one or more of a wireless network interface and a wired network interface. In a third example, I/O device 540 may include one or more of a peripheral component interconnect (PCI) interface, a PCI Express (PCIe) interface, a serial peripheral interconnect (SPI) interface, and an inter-integrated circuit (I$^2$C) interface, among others. In a fourth example, I/O device 540 may include circuitry that may permit processor 510 to communicate data with one or more sensors. In a fifth example, I/O device 540 may facilitate and/or permit processor 510 to communicate data with one or more of a display 550 and a MID 560, among others. In another example, I/O device 540 may facilitate and/or permit processor 510 to communicate data with an imaging device 570. As illustrated, I/O device 540 may be coupled to a network 580. For example, I/O device 540 may include a network interface.

Network 580 may include a wired network, a wireless network, an optical network, or a combination of the foregoing, among others. Network 580 may include and/or be coupled to various types of communications networks. For example, network 580 may include and/or be coupled to a local area network (LAN), a wide area network (WAN), an Internet, a public switched telephone network (PSTN), a cellular telephone network, a satellite telephone network, or a combination of the foregoing, among others. A WAN may include a private WAN, a corporate WAN, a public WAN, or a combination of the foregoing, among others.

A computer system described herein may include one or more structures and/or one or more functionalities as those described with reference to computer system 500. In one example, computer system 250 may include one or more structures and/or one or more functionalities as those described with reference to computer system 500. In a second example, computer system 112 may include one or more structures and/or one or more functionalities as those described with reference to computer system 500. In a third example, computer system 430 may include one or more structures and/or one or more functionalities as those described with reference to computer system 500. In another example, a computer system of MID 450 may include one or more structures and/or one or more functionalities as those described with reference to computer system 500.

Figure 6A:
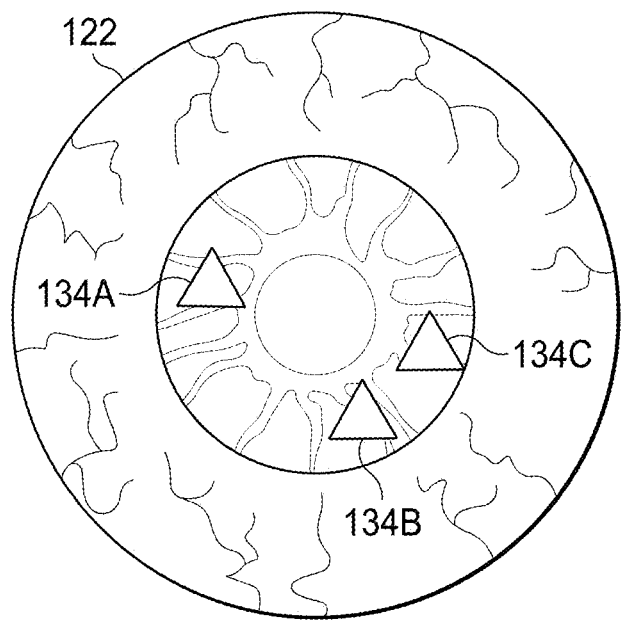
FIGS. 6A-6D illustrate examples of an eye.

Turning now to FIGS. 6A-6D, examples of an eye are illustrated. As shown in FIG. 6A, eye 122 may be oriented upwards. In one example, eye 122 may be oriented upwards without being angled. In another example, eye 122 may be oriented upwards without being rotated. One or more of iris structures 134A-134C may be utilized in determining that eye 122 is oriented upwards. For example, computer system 430 may determine respective positions of the one or more of iris structures 134A-134C. Computer system 430 may determine that eye 122 is oriented upwards based at least on the respective positions of the one or more of iris structures 134A-134C.

Figure 6B:
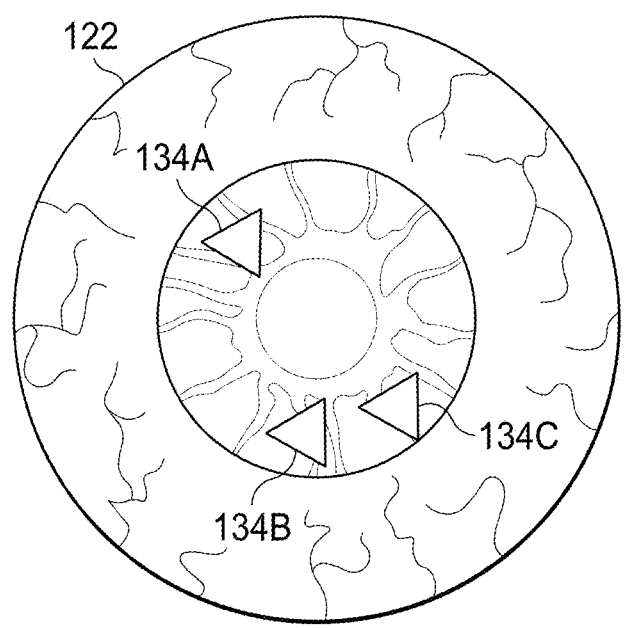

As illustrated in FIG. 6B, eye 122 may be rotated. One or more of iris structures 134A-134C may be utilized in determining that eye 122 is rotated. For example, computer system 430 may determine respective positions of the one or more of iris structures 134A-134C. Computer system 430 may determine that eye 122 is rotated by an angle based at least on the respective positions of the one or more of iris structures 134A-134C.

Figure 6C:
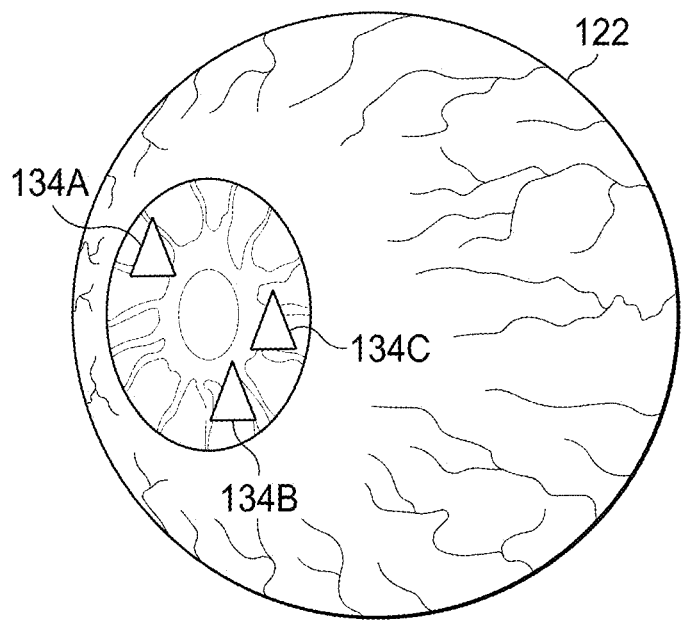

As shown in FIG. 6C, eye 122 may be angled. As illustrated, eye 122 may be angled to the left. One or more of iris structures 134A-134C may be utilized in determining that eye 122 is angled. For example, computer system 430 may determine respective positions of the one or more of iris structures 134A-134C. Computer system 430 may determine that eye 122 is angled by an angle based at least on the respective positions of the one or more of iris structures 134A-134C.

Figure 6D:
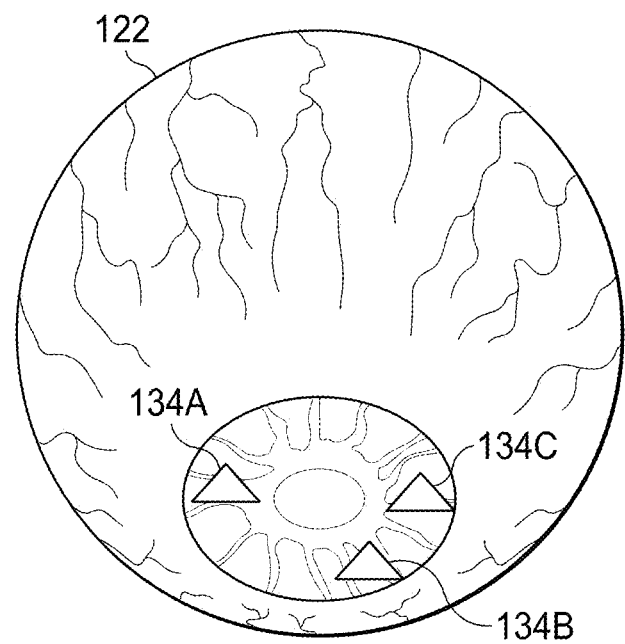

As illustrated in FIG. 6D, eye 122 may be angled. As shown, eye 122 may be angled down. One or more of iris structures 134A-134C may be utilized in determining that eye 122 is angled. For example, computer system 430 may determine respective positions of the one or more of iris structures 134A-134C. Computer system 430 may determine that eye 122 is angled by an angle based at least on the respective positions of the one or more of iris structures 134A-134C.

Figure 6E:
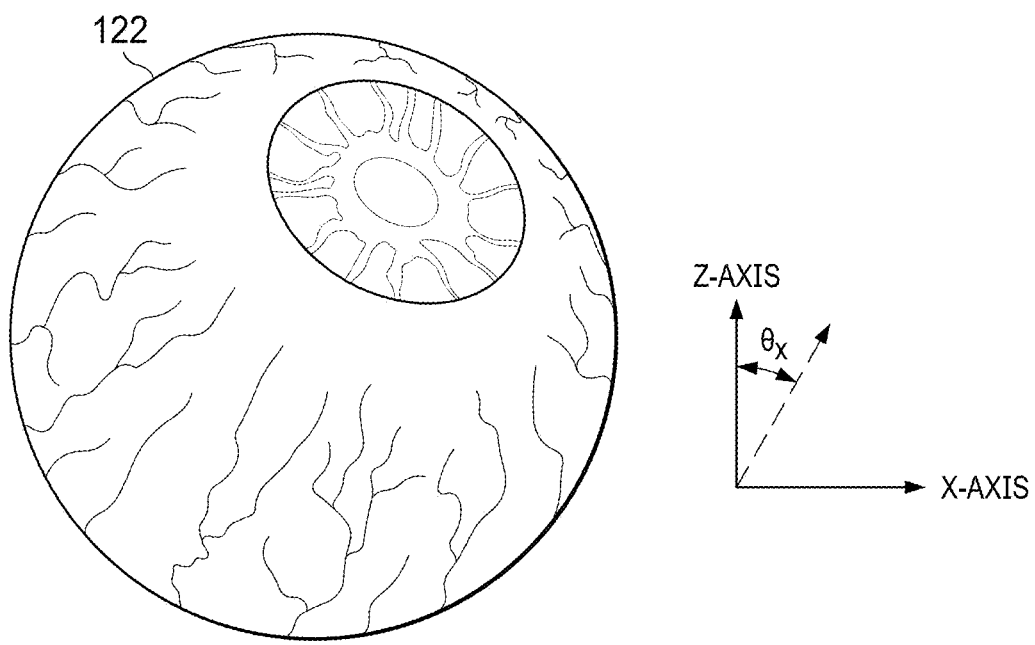
FIGS. 6E-6H illustrate examples of an eye and a coordinate system.
Figure 6F:
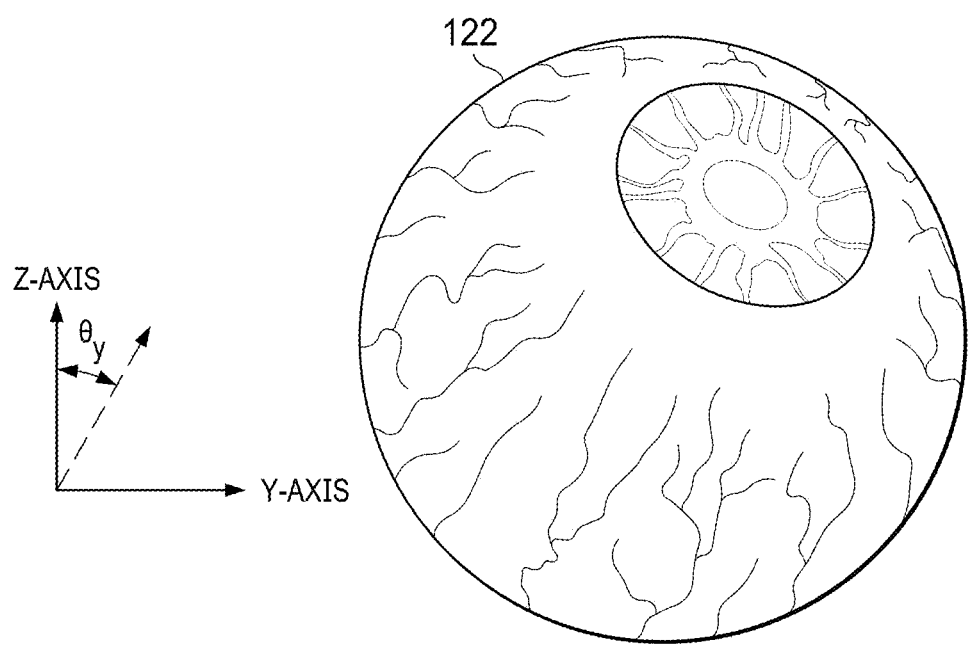
Figure 6G:
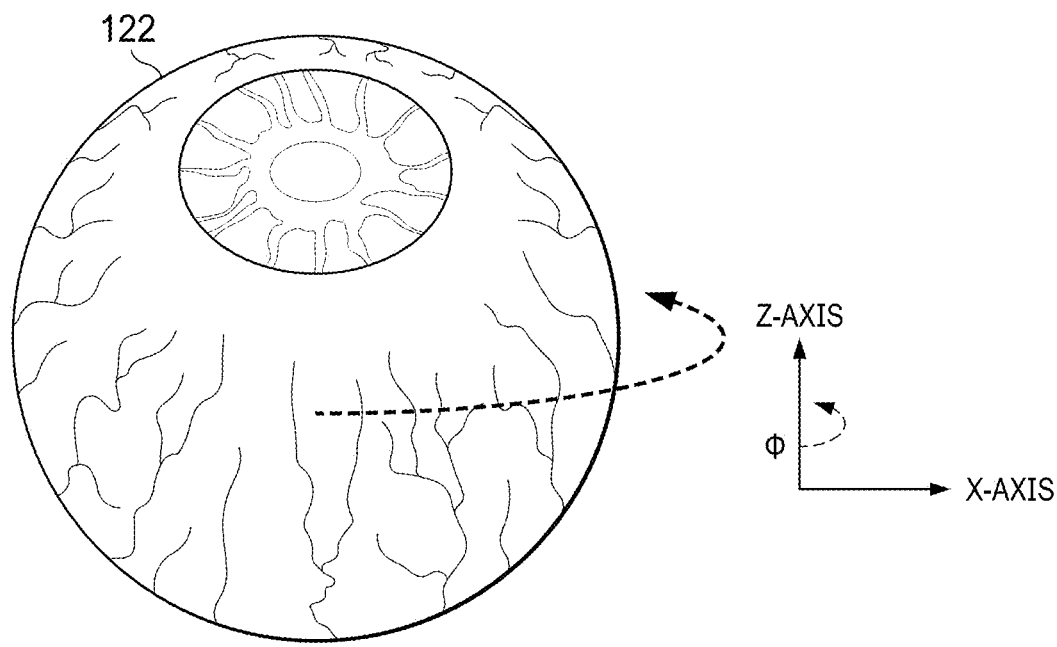
Figure 6H:
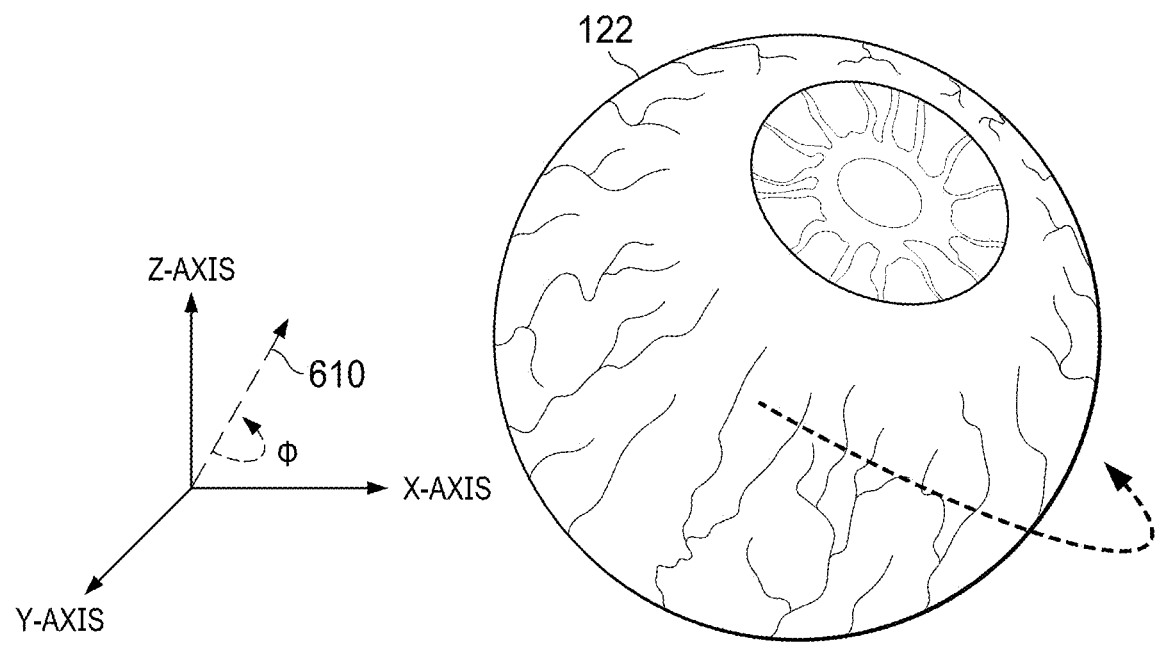

Turning now to FIGS. 6E-6H, examples of an eye and a coordinate system are illustrated. As shown in FIG. 6E, eye 122 may be at an angle $\theta_x$ from a Z-axis with respect to a X-axis. Angle $\theta_x$ may be positive or negative. As illustrated in FIG. 6F, eye 122 may be at an angle $\theta_y$ from the Z-axis with respect to a Y-axis. Angle $\theta_y$ may be positive or negative. As shown in FIG. 6G, eye 122 may be rotated by an angle $\phi$. For example, eye 122 may be rotated by angle $\phi$ about the Z-axis. Angle $\phi$ may be positive or negative. As illustrated in FIG. 6H, eye 122 may be rotated by angle $\phi$ about an arbitrary axis 610. For example, axis 610 may be a vector in a three-dimensional Cartesian coordinate system. Angle $\phi$ may be positive or negative. In one example, axis 610 may be based at least on angle $\theta_x$. In a second example, axis 610 may be based at least on angle $\theta_y$. In another example, axis 610 may be based at least on angle $\theta_x$ and based at least on angle $\theta_y$. Although FIGS. 6E-6H utilize a Cartesian coordinate system, any coordinate system may be utilized. Computer system 430 may determine one or more of angle $\theta_x$, angle $\theta_y$, angle $\phi$, and axis 610 based at least on respective positions of one or more of iris structures 134A-134C.

Figure 7A:
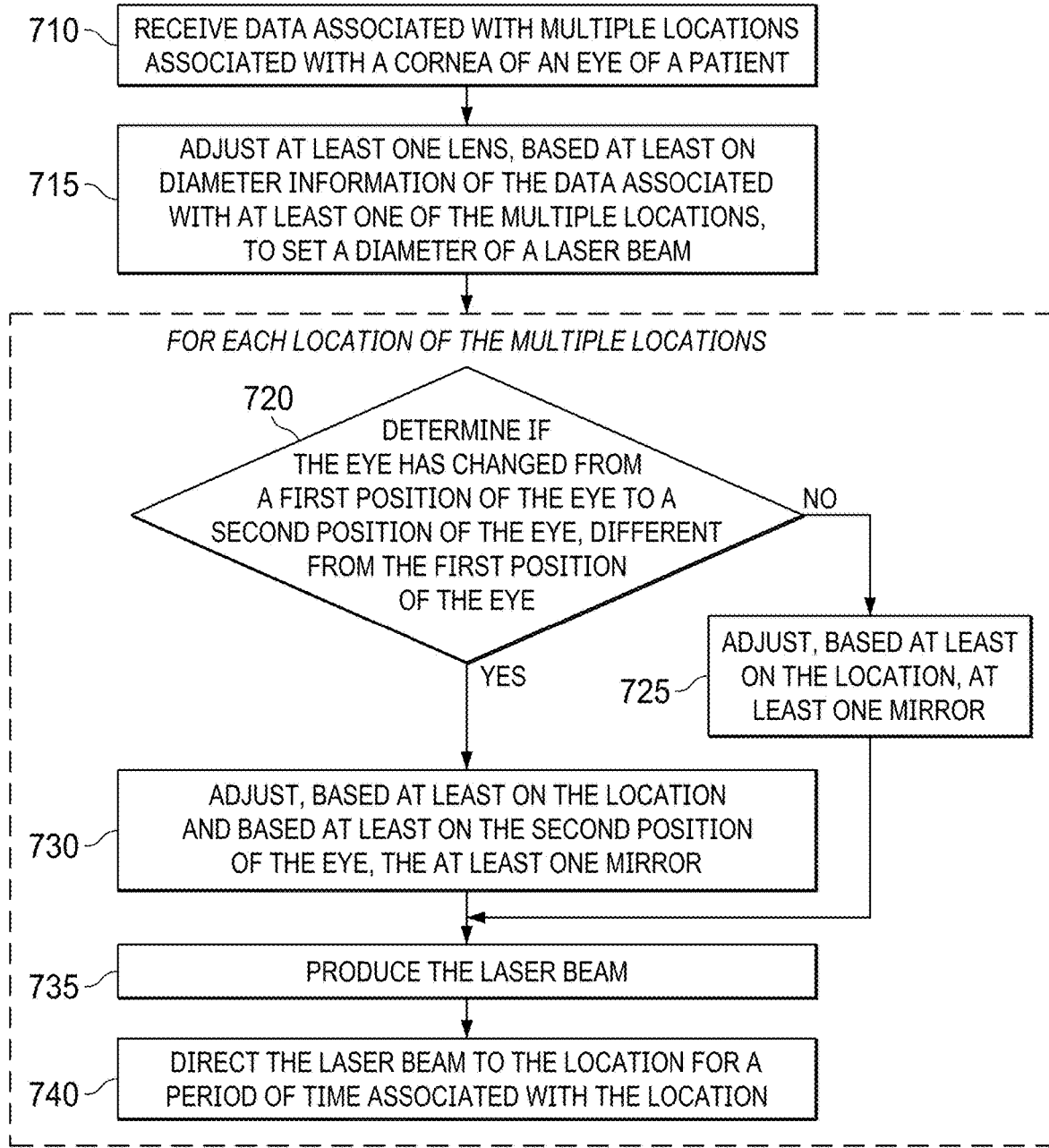
FIG. 7A illustrates an example of a method of operating a medical system.

Turning now to FIG. 7A, an example of a method of operating a medical system is illustrated. At 710, data associated with multiple locations associated with a cornea of an eye of a patient may be received. For example, computer system 430 may receive data 810 (illustrated in FIG. 8) associated with multiple locations 910 associated with cornea 310 of eye 122 of patient 120. Data 810 may include one or more of data 815A-815M, among others. In one example, data 815A-815M may be respectively associated with multiple locations 910A-910M. In a second example, data 815A may be associated with location 910, illustrated in FIG. 9C. In another example, data 815A may be associated with location 910, illustrated in FIG. 9C, and data 815B and 815C may be respectively associated with locations 910A and 910B, any of illustrated in FIGS. 9D-9F. The data associated with the multiple locations, associated with the cornea of the eye of the patient, may include locations 910 of any of FIGS. 9C-9F. For example, multiple data 815 may be utilized in any order. Data associated with locations 910A-910G, illustrated in any of FIGS. 9D-9F, may be utilized before data associated with location 910, illustrated in FIG. 9C. Data associated with location 910, illustrated in FIG. 9C, may be utilized before data associated with locations 910A-910G, illustrated in any of FIGS. 9D-9F. For example, one or more locations of a FIG. of FIGS. 9C-9F may be irritated with a laser beam before another FIG. of FIGS. 9C-9F may be irritated with a laser beam. Data 810 may include information that may described, characterize, and/or indicate this performance.

Figure 9A:
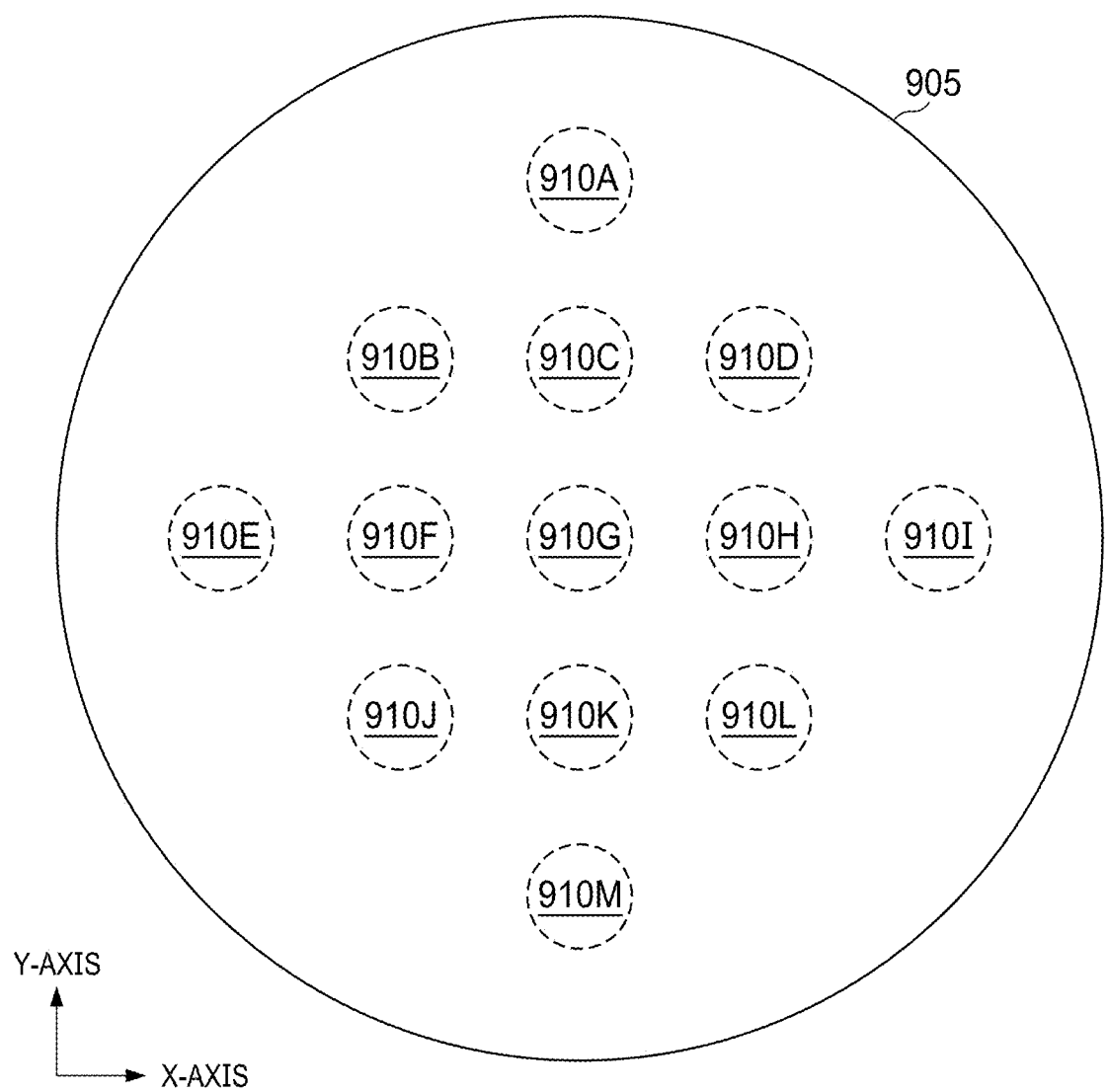
FIG. 9A illustrates an example of a plane and multiple locations.
Figure 9B:
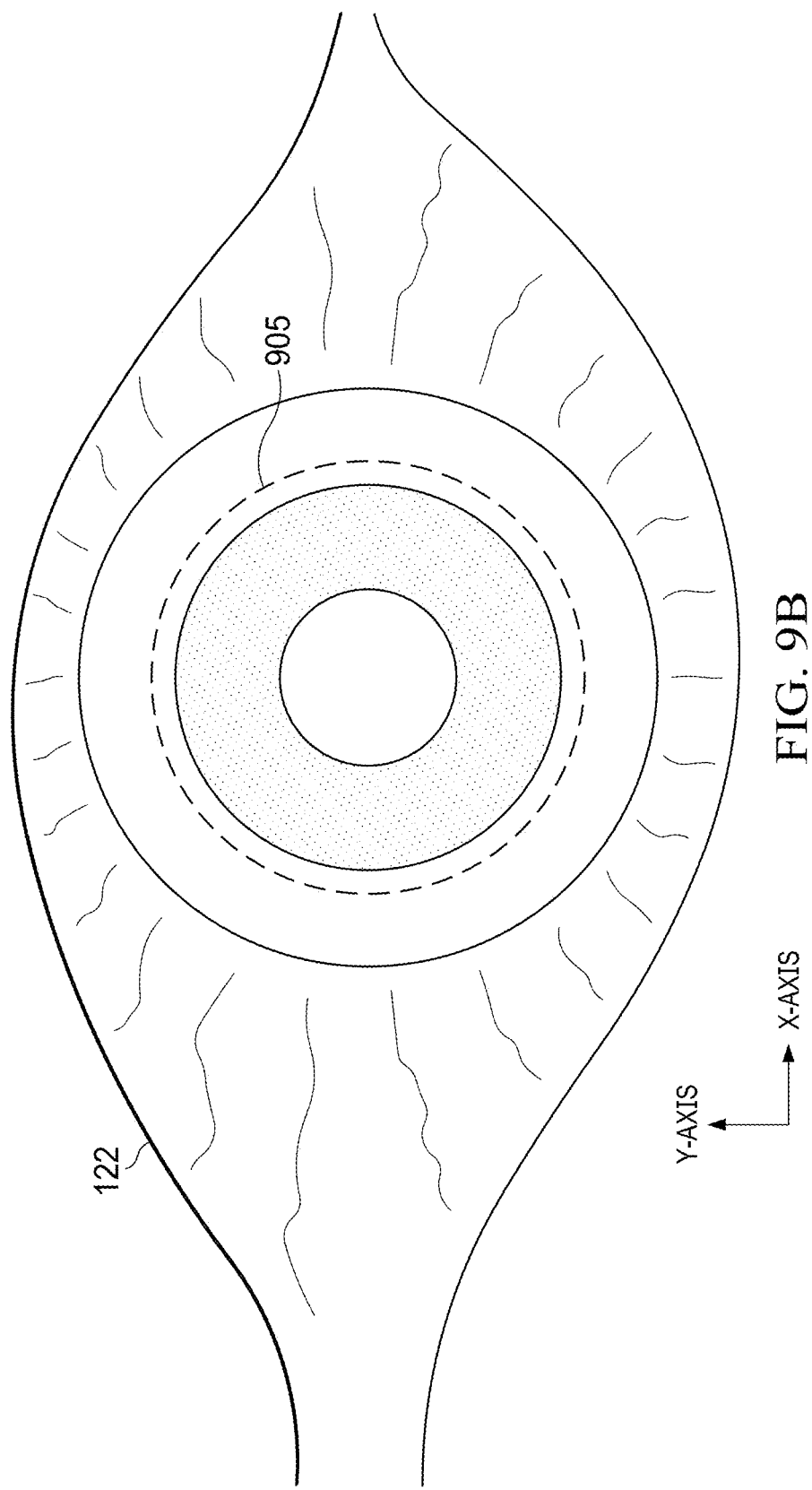
FIG. 9B illustrates an example of a plane associated with an eye.

As illustrated in FIG. 9A, a plane 905 may be associated with multiple locations 910A-910M. Plane 905 may be orthogonal to laser 221 after laser 221 is transmitted from objective lens 248. Plane 905 may be associated with eye 122 as illustrated in FIG. 9B. Multiple locations 910A-910M may be associated with cornea 310 of eye 122 of patient 120. Although only fourteen locations are illustrated in FIG. 9A, any number of locations may be utilized.

Figure 9C:
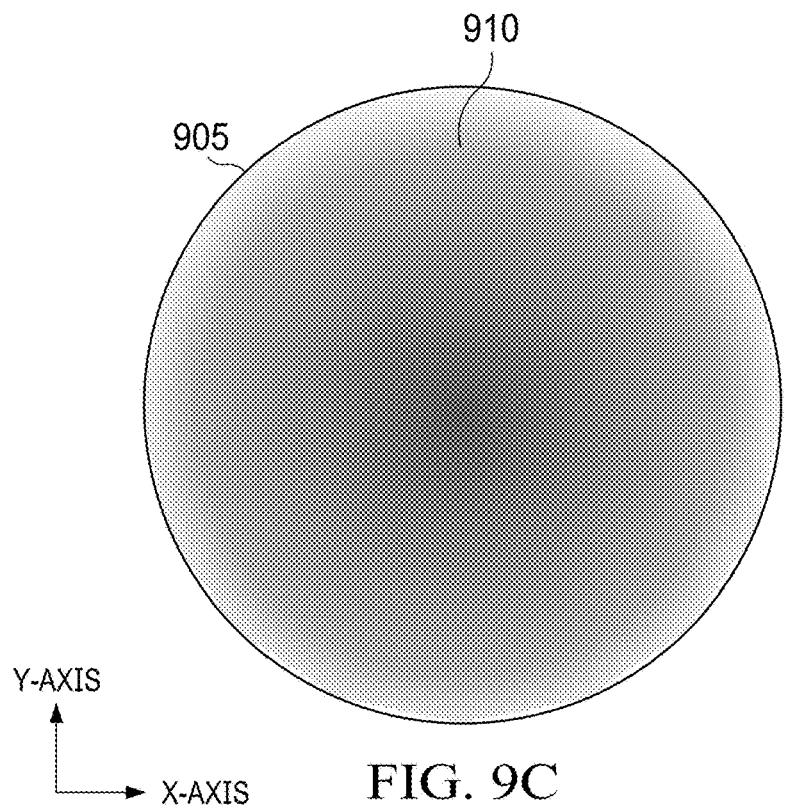
FIG. 9C illustrates an example of a location associated with a plane.
Figure 9D:
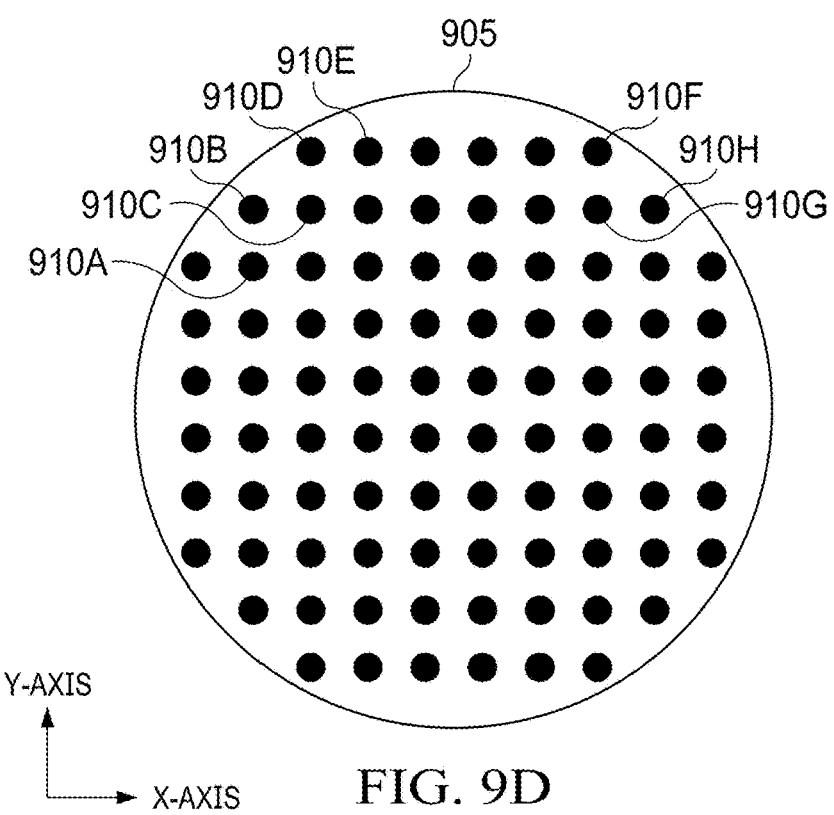
FIG. 9D illustrates an example of multiple locations associated with a plane.
Figure 9E:
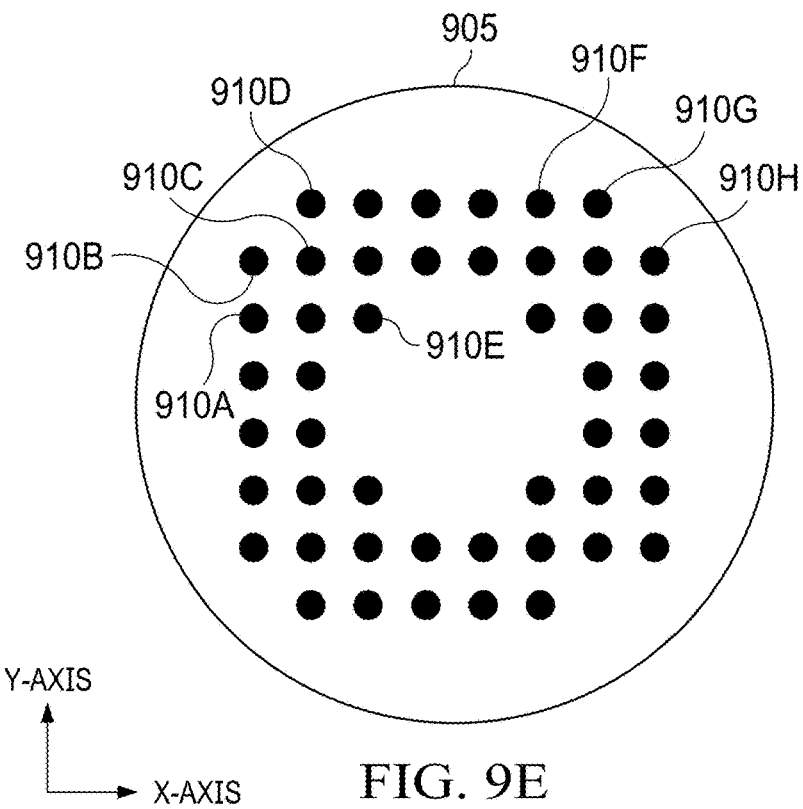
FIG. 9E illustrates a second example of multiple locations associated with a plane.
Figure 9F:
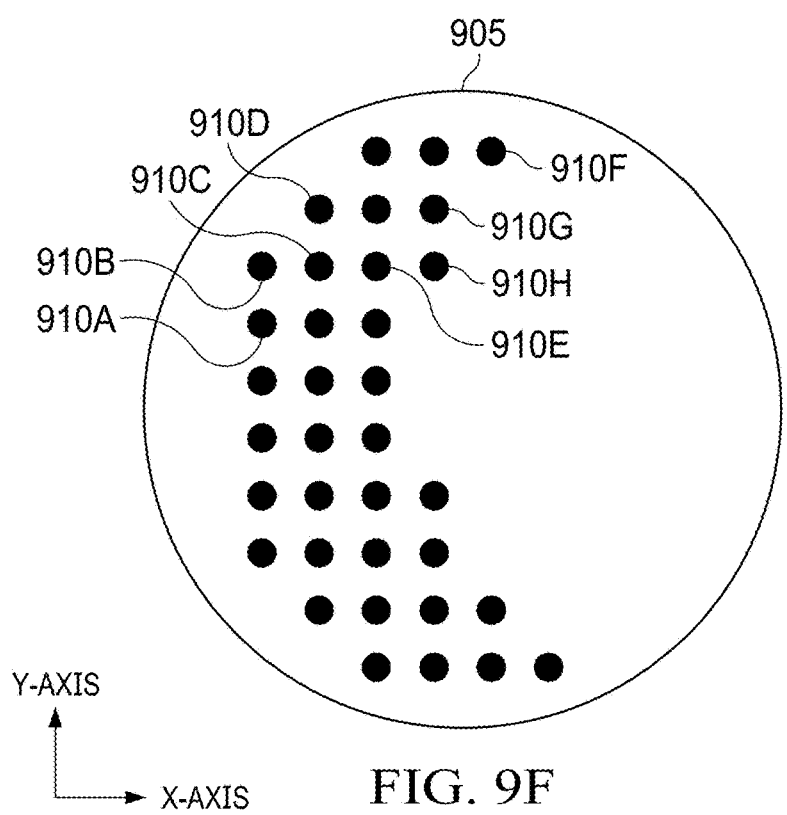
FIG. 9F illustrates another example of multiple locations associated with a plane.
Figure 9G:
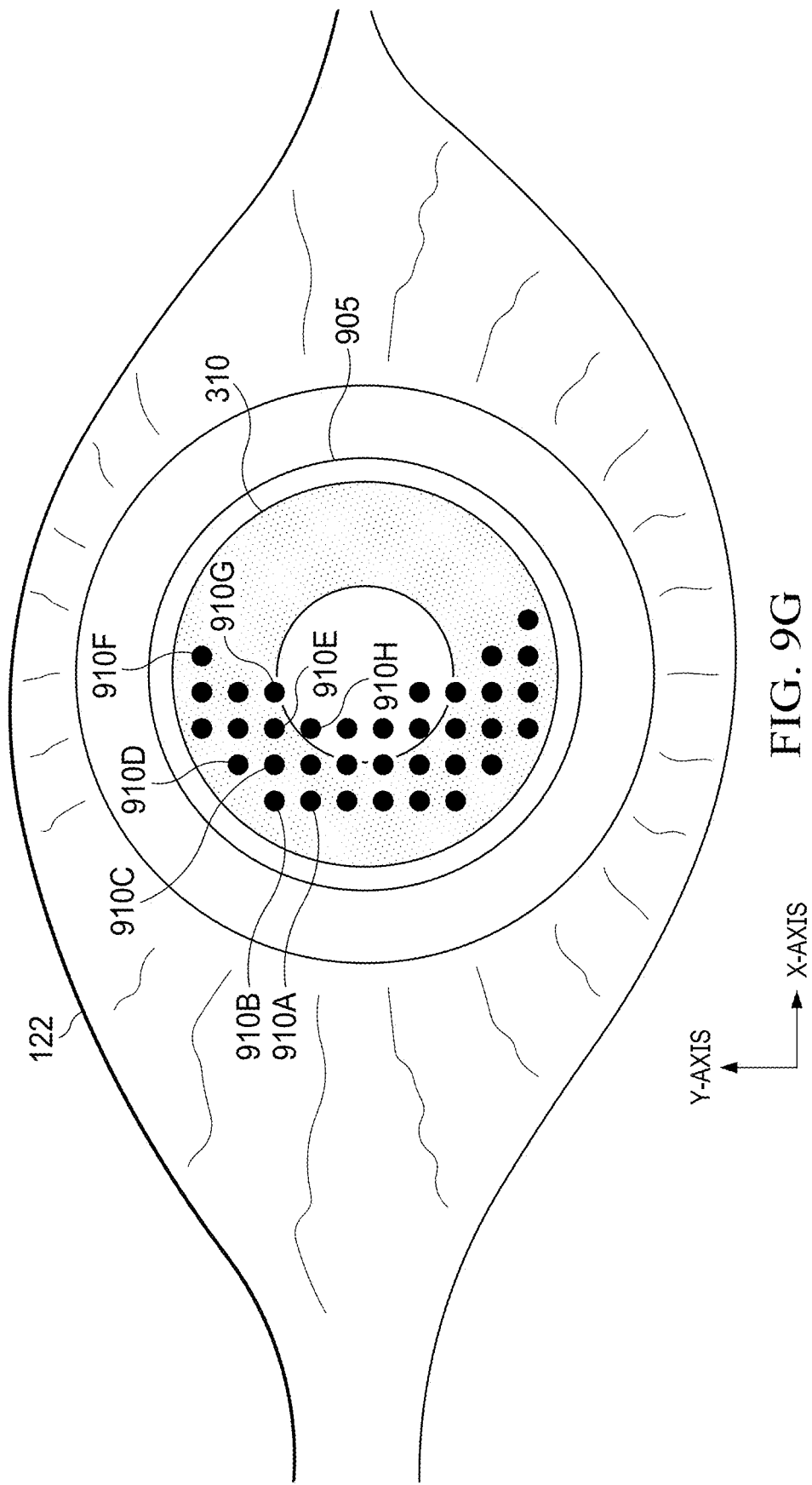
FIG. 9G illustrates an example of multiple locations associated with a plane and a cornea.
Figure 9H:
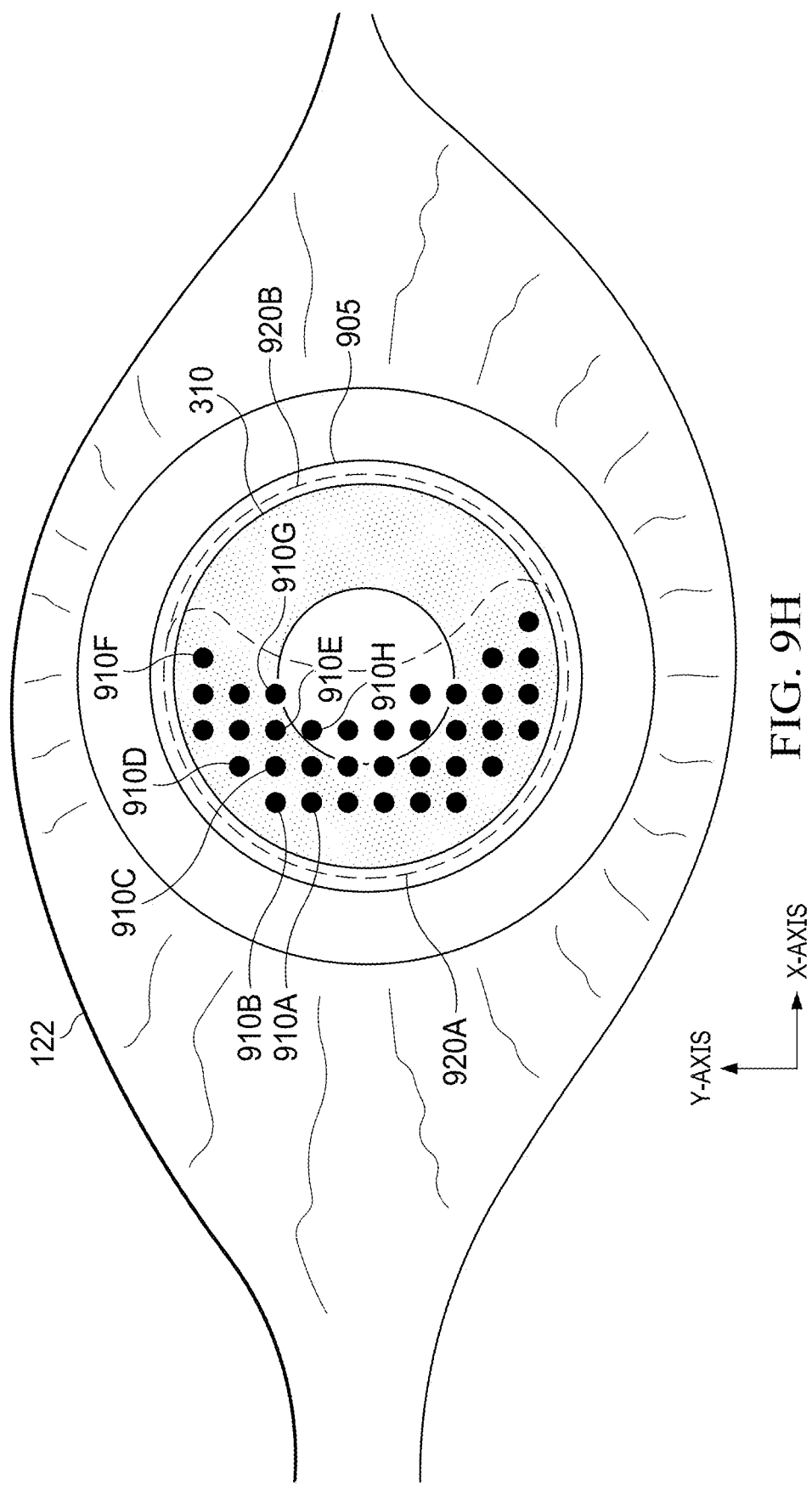
FIG. 9H illustrates an example of a portion of a cornea associated multiple locations.

Furthermore, locations 910 may be arranged at any locations. In one example, a single location 910 is illustrated in FIG. 9C. In a second example, multiple locations 910 may be associated with plane 905 as illustrated in FIG. 9D. In a third example, multiple locations 910 may be associated with plane 905 as illustrated in FIG. 9E. In another example, multiple locations 910 may be associated with plane 905 as illustrated in FIG. 9F. As illustrated in FIG. 9G, multiple locations 910 may be associated with cornea 310 of eye 122. As shown in FIG. 9F, a first portion of cornea 310 is associated with locations 910. As illustrated in FIG. 9F, a second portion of cornea 310, different from first portion, is not associated with locations 910. For example, one or more portions of cornea 310 may be treated while one or more other one or more portions of cornea 310 may not be treated.

Figure 8:
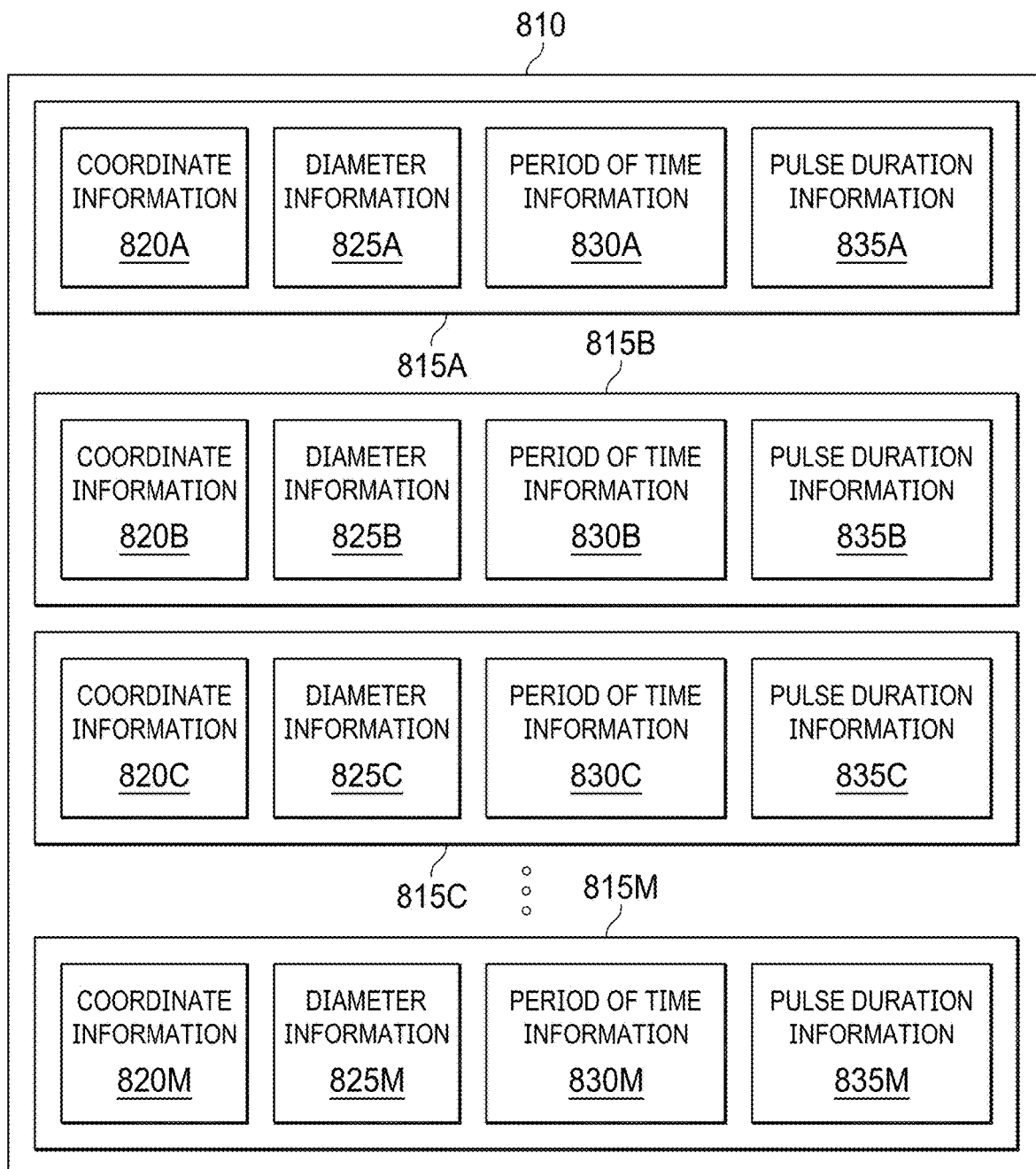
FIG. 8 illustrates an example of data associated with multiple locations associated with a cornea of an eye of a patient.

As illustrated in FIG. 8, data 810 may include data 815A-815M. For example, data 815A-815M may be respectively associated with locations 910A-910M. Data 815 may include coordinate information 820. For example, coordinate information 820 may include XY coordinates. The XY coordinates may be associated with a X-axis and a Y-axis. Data 815 may include diameter information 825. For example, diameter information 825 may include a diameter measurement of a laser beam associated with location 910. Data 815 may include period of time information 830. For example, period of time information 830 may include a period of time to apply a laser beam at location 910. Data 815 may include pulse duration information 835. For example, pulse duration information 835 may include a pulse duration. As an example, a pulse duration may include a microsecond duration, a nanosecond duration, a picosecond duration, a femtosecond duration, or an attosecond duration, among others. For example, laser 220 may be configured with a pulse duration based at least on pulse duration information 835.

At 715, at least one lens may be adjusted based at least on diameter information of the data associated with at least one of the multiple locations, to set a diameter of a laser beam. For example, at least one of lenses 242A and 242B may be adjusted based at least on diameter information of the data associated with at least one of the multiple locations, to set a diameter of laser beam 221. A computer system may provide control information to beam expander 241 to adjust at least one of lenses 242A and 242B to set a diameter of laser beam 221. In one example, computer system 250 may provide control information to beam expander 241 to adjust at least one of lenses 242A and 242B to set a diameter of laser beam 221. In a second example, computer system 430 may provide control information to beam expander 241 to adjust at least one of lenses 242A and 242B to set a diameter of laser beam 221. In a third example, computer system 430 may provide control information to computer system 250. Computer system 250 may provide the control information to beam expander 241 to adjust at least one of lenses 242A and 242B to set a diameter of laser beam 221. In another example, computer system 430 may be or include computer system 250. The control information may be based at least on the diameter information of the data associated with the at least one of the multiple locations.

Method elements 720-740 may be performed for each of the multiple locations associated with the cornea of the eye of the patient. For example, Method elements 720-740 may be performed for each of multiple locations 910.

At 720, it may be determined if the eye has changed from a first position of the eye to a second position of the eye, different from the first position of the eye. For example, computer system 430 may determine if eye 122 has changed from a first position of the eye to a second position of the eye, different from the first position of the eye. As one example, eye 122 may change from a first position of eye 122, illustrated in FIG. 6A, to a second position of eye 122, illustrated in FIG. 6B. Eye 122 may have changed from the first position of eye 122, illustrated in FIG. 6A, to the second position of eye 122, illustrated in FIG. 6B, via one or more rotations. As a second example, eye 122 may change from a first position of eye 122, illustrated in FIG. 6A, to a second position of eye 122, illustrated in FIG. 6C. As a third example, eye 122 may change from a first position of eye 122, illustrated in FIG. 6A, to a second position of eye 122, illustrated in FIG. 6D. As another example, eye 122 may change from a first position of eye 122, illustrated in FIG. 6C, to a second position of eye 122, illustrated in FIG. 6D. Determining if the eye has changed from the first position of the eye to the second position of the eye, different from the first position of the eye, may include determining if a pupil of the eye has changed from a first position of the pupil to a second position of the pupil. Determining if the eye has changed from the first position of the eye to the second position of the eye, different from the first position of the eye, may include determining if a center of a pupil of the eye has changed from a first position of the center of the pupil to a second position of the center of the pupil.

Determining if the eye has changed from the first position of the eye to the second position of the eye, different from the first position of the eye, may include determining if at least one iris structure has changed from a first position of the at least one iris structure to a second position of the at least one iris structure. In one example, iris structure 134A may be at a first position of iris structure 134A, illustrated in FIG. 6A, and iris structure 134A may be at a second position of iris structure 134A, illustrated in FIG. 6B. In a second example, iris structure 134A may be at a first position of iris structure 134A, illustrated in FIG. 6A, and iris structure 134A may be at a second position of iris structure 134A, illustrated in FIG. 6C. In a third example, iris structure 134A may be at a first position of iris structure 134A, illustrated in FIG. 6A, and iris structure 134A may be at a second position of iris structure 134A, illustrated in FIG. 6D. In another example, iris structure 134A may be at a first position of iris structure 134A, illustrated in FIG. 6C, and iris structure 134A may be at a second position of iris structure 134A, illustrated in FIG. 6D. In these examples, one or more of iris structures 134B and 134C may be utilized in place of or in addition to iris structure 134A in a fashion as iris structure 134A has been described. As one example, one or more of iris structures 134A-134C may be determined via medical system 110. As another example, one or more of iris structures 134A-134C may be determined via medical system 400.

If the eye has not changed from a first position of the eye to a second position of the eye, at least one mirror may be adjusted based at least on the location, at 725. For example, if eye 122 has not changed from a first position of eye 122 to a second position of eye 122, at least one mirror of scanner 244 may be adjusted based at least on location 910. For example, scanner 244 may include one or more mirrors that may be adjusted based at least on location 910.

If the eye has changed from the first position of the eye to the second position of the eye, the at least one mirror may be adjusted based at least on the location and based at least on the second position of the eye, at 730. For example, if eye 122 has changed from the first position of eye 122 to the second position of eye 122 at least one mirror of scanner 244 may be adjusted based at least on location 910 and based at least on the second position of eye 122. As an example, scanner 244 may include one or more mirrors that may be adjusted based at least on location 910 and based at least on the second position of eye 122.

If eye 122 has changed from the first position of the eye to the second position of the eye, location 910 may be translated based at least on the second position of the eye. Adjusting the at least one mirror based at least on the location and based at least on the second position of the eye may include adjusting the at least one mirror based at least on the location and based at least on a translation of the location. The translation may be based at least on the second position of the eye. In one example, translating based at least on the second position may include translating based at least on a second position of a center of a pupil of eye 122. In a second example, translating based at least on the second position of the eye may include translating based at least on a second position of an iris structure. The second position of the iris structure may be a second position of iris structure 134A, a second position of iris structure 134B, or a second position of iris structure 134C, among others. In another example, translating based at least on the second position of the eye may include translating based at least on second positions of respective multiple iris structures. The second positions of the respective multiple iris structures may include two or more of a second position of iris structure 134A, a second position of iris structure 134B, and a second position of iris structure 134C, among others.

A computer system may compute one or more translations of one or more locations 910. For example, the computer system may compute a translation of a location 910 based at least on one or more of angle $\theta_x$, angle $\theta_y$, angle $\phi$, and axis 610, among others. A computer system may determine one or more of angle $\theta_x$, angle $\theta_y$, angle $\phi$, and axis 610 based at least on respective positions of one or more of iris structures 134A-134C. In one example, the computer system may determine one or more of angle $\theta_x$, angle $\theta_y$, angle $\phi$, and axis 610 based at least on a first position of iris structure 134A and a second position of iris structure 134A. In a second example, the computer system may determine one or more of angle $\theta_x$, angle $\theta_y$, angle $\phi$, and axis 610 based at least on a first position of iris structure 134B and a second position of iris structure 134B. In another example, the computer system may determine one or more of angle $\theta_x$, angle $\theta_y$, angle $\phi$, and axis 610 based at least on a first position of iris structure 134C and a second position of iris structure 134C.

At 735, the laser beam may be produced. For example, laser 220 may produce laser beam 221. Laser beam 221 may be an UV laser beam. For example, laser 220 may be or include a device that generates a beam of coherent monochromatic light, in an UV spectrum, by stimulated emission of photons from excited atoms and/or molecules. Producing the laser beam may include pulsing the laser beam at a pulse duration. For example, the pulse duration may be a microsecond duration, a nanosecond duration, a picosecond duration, a femtosecond duration, or an attosecond duration, among others. The pulse duration may be configured and/or set based at least on pulse duration information 835 associated with location 910. In one example, the pulse duration may be configured and/or set based at least on pulse duration information 835A associated with location 910A. In another example, the pulse duration may be configured and/or set based at least on pulse duration information 835B associated with location 910B. A first pulse duration, associated with a first location, may be different from a second pulse duration, associated with a second location. The pulse duration associated with location 910A may be different from the pulse duration associated with location 910B. The pulse duration associated with location 910A may be equal to the pulse duration associated with location 910B.

Before the laser beam is produced, at least one of a flap and a pocket may be cut in the cornea of the eye. In one example, a blade may cut the cornea of the eye. In another example, another laser may cut the cornea of the eye. Before the laser beam is produced, riboflavin may be applied to an interior portion of the cornea. For example, riboflavin may be applied to an interior portion of the cornea via the flap that was cut or via the pocket that was cut. Before the laser beam is produced, a layer of the cornea may be removed to expose an interior portion of the cornea. Layer 320, as illustrated in FIG. 3, may be removed. Riboflavin may applied to the cornea after the layer of the cornea is removed and before the laser beam is produced.

At 740, the laser beam may be directed to the location for a period of time associated with the location. For example, laser beam 221 may be directed to location 910 for a period of time associated with location 910. Focusing optics 240 may direct laser beam 221 to location 910 for a period of time associated with location 910. A first period of time associated with a first location may be different from a second period of time associated with a second location. For example, a period of time associated with location 910A may be different from a period of time associated with location 910B. The period of time associated with location 910A may be indicated by period of time information 830A. The period of time associated with location 910B may be indicated by period of time information 830B. A period of time associated with a first location may be equal a second period of time associated with a second location. For example, a period of time associated with location 910A may be equal to a period of time associated with location 910B.

Directing the laser beam to the location for the period of time associated with the location may add bonds between collagen fibers in the cornea. For example, directing laser beam 221 to location 910 for the period of time associated with location 910 may add bonds between collagen fibers in cornea 310 associated with location 910.

The bonds between the collagen fibers may aid in stabilizing cornea 310. For example, the bonds between the collagen fibers associated with each location of locations 910 may aid in stabilizing cornea 310. Locations 910 may be determined based at least on a topography of cornea 310. Locations 910 may be determined based at least on a thicknesses at respective multiple positions associated with cornea 310. Locations 910 may be determined based at least on refractive information associated with one or more of cornea 310 and eye 122, among others. For example, one or more of methods 7A and 7B, among others, may be utilized in correcting an astigmatism in cornea 310. Locations 910 may be determined based at least on a medical plan that may mitigate or may stop an issue and/or a disease that may weaken and/or thin cornea 310. For example, locations 910 may be determined based at least on a medical plan that may mitigate or may stop progressive keratoconus from becoming worse.

Figure 7B:
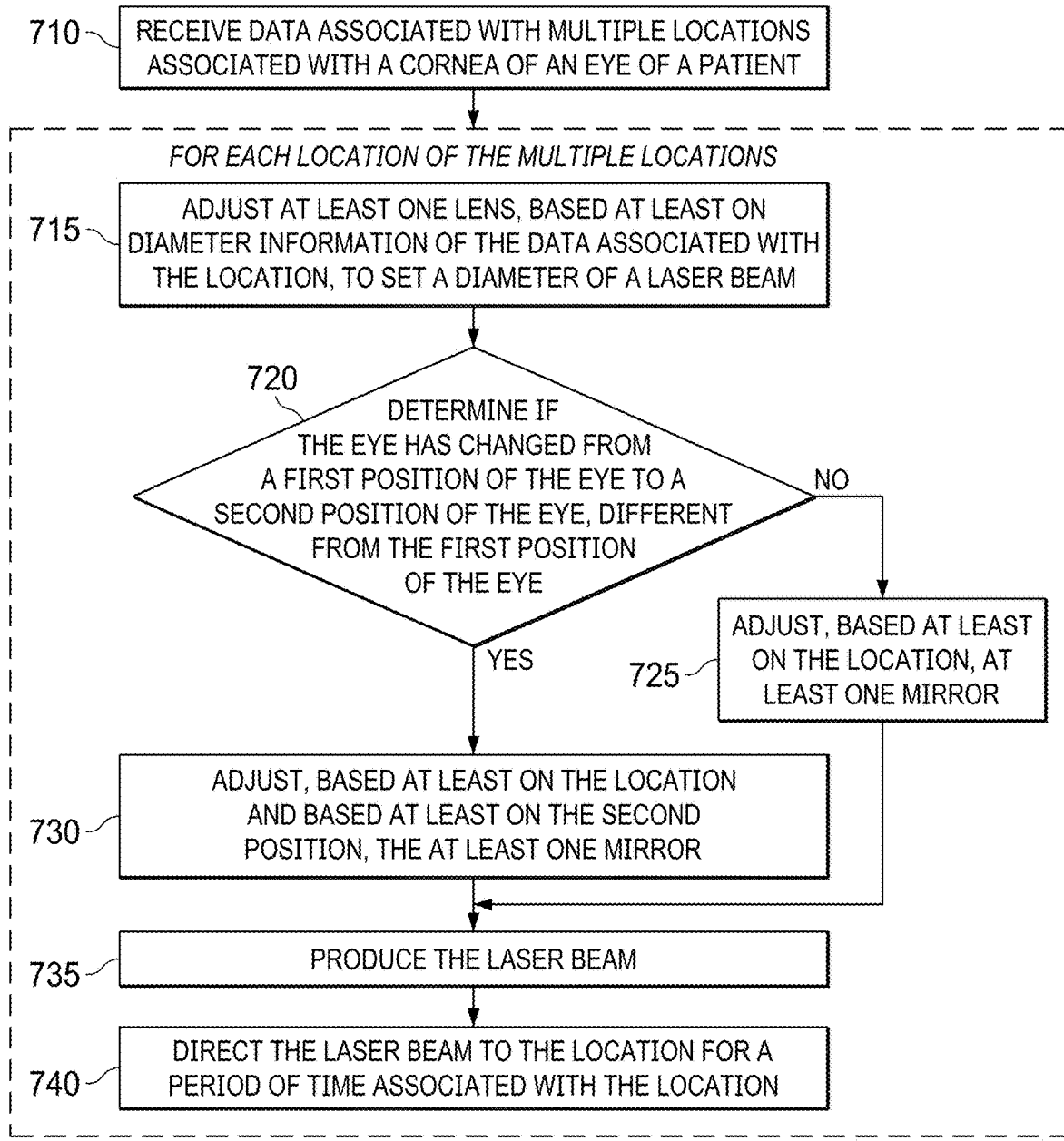
FIG. 7B illustrates another example of a method of operating a medical system.

Turning now to FIG. 7B, another example of a method of operating a medical system is illustrated. Method elements 710 and 720-740 may be performed as described with reference to FIG. 7A. In the method associated with FIG. 7B, method elements 715-740 may be performed for each of the multiple locations associated with the cornea of the eye of the patient. For example, method elements 715-740 may be performed for each of multiple locations 910. At 715, at least one lens may be adjusted, based at least on diameter information of the data associated with the location, to set a diameter of a laser beam.

At least a first diameter associated with a first location may be different from a second diameter associated with a second location. In one example, a diameter associated with location 910A may be different from a diameter associated with location 910B. Diameter information 825A may indicate the diameter associated with location 910A. Diameter information 825B may indicate the diameter associated with location 910B. In a second example, a diameter associated with location 910A may be different from a diameter associated with location 910C. Diameter information 825A may indicate the diameter associated with location 910A. Diameter information 825C may indicate the diameter associated with location 910C. In another example, a diameter associated with location 910A may be equal to a diameter associated with location 910D. Diameter information 825A may indicate the diameter associated with location 910A. Diameter information 825D may indicate the diameter associated with location 910D.

One or more of the method and/or process elements and/or one or more portions of a method and/or processor elements may be performed in varying orders, may be repeated, or may be omitted. Furthermore, additional, supplementary, and/or duplicated method and/or process elements may be implemented, instantiated, and/or performed as desired. Moreover, one or more of system elements may be omitted and/or additional system elements may be added as desired.

A memory medium may be and/or may include an article of manufacture. For example, the article of manufacture may include and/or may be a software product and/or a program product. The memory medium may be coded and/or encoded with processor-executable instructions in accordance with one or more flowcharts, systems, methods, and/or processes described herein to produce the article of manufacture.

The above disclosed subject matter is to be considered illustrative, and not restrictive, and the appended claims are intended to cover all such modifications, enhancements, and other implementations which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A medical system, comprising:
   at least one processor;
   a camera configured to generate image data for an image of an eye of a patient;
   a laser that is communicatively coupled to the at least one processor and that is configured to produce one or more laser beams along a Z-axis;
   at least one lens;
   at least one mirror; and
   a memory medium that is coupled to the at least one processor and that includes instructions that, when executed by the at least one processor, cause the medical system to:
   receive data and a plurality of intensity profiles associated with a plurality of locations of a cornea of the eye of the patient, the locations comprising a first location and a second location different from the first location, the first location associated with a first intensity profile, the second location associated with a second intensity profile, the first intensity profile providing a greater optical intensity than the second intensity profile to enhance a corneal cross-linking (CXL) effect, the data comprising for each of the plurality of locations: coordinate information, diameter information, period of time information, and pulse duration information;
   adjust the at least one lens, based at least on the diameter information of the data associated with at least one location to set a diameter of a laser beam; and
   perform, for each location of the plurality of locations, according to at least the data and the intensity profile for the location:
   determine if the eye has changed from a first position of the eye to a second position of the eye, different from the first position of the eye;
   performing at least one of:
   if the eye has not changed from the first position of the eye to the second position of the eye, adjust the at least one mirror according to at least the data for the location;
   if the eye has changed from the first position of the eye to the second position of the eye, adjust the at least one mirror according to at least the data for the location and the second position of the eye, the data for the location comprising coordinate information, wherein the coordinate information comprises an X-axis, a Y-axis, the Z-axis, an angle $\theta_X$ measured from the Z-axis to the X-axis, an angle $\theta_Y$ measured from the Z-axis to the Y-axis, and a rotation angle $\phi$ measuring rotation about the Z-axis;
   produce the laser beam;
   direct the laser beam to the location according to the intensity profile and the period of time information associated with the location; and
   identify an eye dropper in the image of the eye according to a pattern marking the eye dropper, the pattern comprising a fractal pattern that identifies the eye dropper, the eye dropper configured to dispense riboflavin onto the cornea to enhance the CXL effect.

2. The medical system of claim 1, wherein, to determine if the eye has changed from the first position of the eye to the second position of the eye, the instructions further cause the medical system to determine if an iris structure of the eye has changed from a first position of the iris structure to a second position of the iris structure.

3. The medical system of claim 1, wherein a first period of time associated with the first location is different from a second period of time associated with the second location.

4. The medical system of claim 1, wherein, to produce the laser, the instructions further cause the medical system to pulse the laser beam at a pulse duration.

5. The medical system of claim 4, wherein the pulse duration is a microsecond duration, a nanosecond duration, a picosecond duration, a femtosecond duration, or an attosecond duration.

6. The medical system of claim 1, wherein the laser beam is an ultraviolet (UV) laser beam.

7. The medical system of claim 1, wherein the instructions further cause the medical system to:
   adjust the at least one lens, based at least on second diameter information of the data associated with at least another one of the plurality of locations, to set a second diameter of the laser beam.

8. The medical system of claim 1, wherein the instructions further cause the medical system to:
before the laser beam is produced, produce another laser beam to cut at least one of a flap and a pocket in the cornea.

9. The medical system of claim 1:
further comprising an illuminator configured to provide ultraviolet light; and
the pattern comprising dye or paint that reflects ultraviolet light.

10. The medical system of claim 1:
further comprising an illuminator configured to provide infrared light; and
the pattern comprising dye or paint that reflects infrared light.

11. The medical system of claim 1:
the pattern comprising a hash pattern that identifies the eye dropper.

12. A method of operating a medical system, comprising:
receiving data and a plurality of intensity profiles associated with a plurality of locations of a cornea of an eye of a patient, the locations comprising a first location and a second location, the first location associated with a first intensity profile, the second location associated with a second intensity profile, the first intensity profile providing a greater optical intensity that the second intensity profile to enhance a corneal cross-linking (CXL) effect, the data comprising for each of the plurality of locations: coordinate information, diameter information, period of time information, and pulse duration information;
adjusting at least one lens, based at least on diameter information of the data associated with at least one location, to set a diameter of a laser beam; and
performing for each location of the plurality of locations, according to at least the data for the location:
determining if the eye has changed from a first position of the eye to a second position of the eye, different from the first position of the eye;
performing at least one of:
if the eye has not changed from the first position of the eye to the second position of the eye, adjusting at least one mirror according to at least the data for the location;
if the eye has changed from the first position of the eye to the second position of the eye, adjusting the at least one mirror according to at least the data for the location and the second position of the eye, the data for the location comprising coordinate information, wherein the coordinate information comprises an X-axis, a Y-axis, a Z-axis, an angle $\theta_X$ measured from the Z-axis to the X-axis, an angle $\theta_Y$ measured from the Z-axis to the Y-axis, and a rotation angle $\phi$ measuring rotation about the Z-axis;
producing the laser beam; and
directing the laser beam to the location according to the intensity profile and the period of time information associated with the location;
generating an image of the eye; and
identifying an eye dropper in the image of the eye of the patient according to a pattern marking surgical tooling equipment, the pattern comprising a fractal pattern that identifies the eye dropper, the eye dropper configured to dispense riboflavin onto the cornea to enhance the CXL effect.

13. The method of claim 12, wherein the determining if the eye has changed from the first position of the eye to the second position of the eye includes determining if an iris structure of the eye has changed from a first position of the iris structure to a second position of the iris structure.

14. The method of claim 12, wherein a first period of time associated with the first location is different from a second period of time associated with the second location.

15. The method of claim 12, wherein the producing the laser includes pulsing the laser beam at a pulse duration.

16. The method of claim 15, wherein the pulse duration is a microsecond duration, a nanosecond duration, a picosecond duration, a femtosecond duration, or an attosecond duration.

17. The method of claim 12, wherein the laser beam is an ultraviolet (UV) laser beam.

18. The method of claim 12, further comprising:
adjusting the at least one lens, based at least on second diameter information of the data associated with at least another one of the plurality of locations, to set a second diameter of the laser beam.

19. The method of claim 12,
before the producing the laser beam, producing another laser beam to cut at least one of a flap and a pocket in the cornea.

* * * * *